(12) United States Patent
Martens et al.

(10) Patent No.: US 11,672,615 B2
(45) Date of Patent: Jun. 13, 2023

(54) MAGNETIC FIELD PROBE FOR DETERMINING A DISPOSITION OF AN IMPLANTABLE MARKER USING TWO OR MORE DETECTION ZONES

(71) Applicant: SIRIUS MEDICAL SYSTEMS B.V., Eindhoven (NL)

(72) Inventors: Hubert Martens, Eindhoven (NL); Bram Schermers, Eindhoven (NL); Takeshi Kaneko, Eindhoven (NL); Pietro Falgari, Eindhoven (NL)

(73) Assignee: SIRIUS MEDICAL SYSTEMS B.V., Eindhoven (NL)

( * ) Notice: Subject to any disclaimer, the term of this patent is extended or adjusted under 35 U.S.C. 154(b) by 0 days.

(21) Appl. No.: 17/841,212

(22) Filed: Jun. 15, 2022

(65) Prior Publication Data

US 2022/0323160 A1    Oct. 13, 2022

Related U.S. Application Data

(63) Continuation of application No. PCT/IB2020/062259, filed on Dec. 20, 2020.

(30) Foreign Application Priority Data

Dec. 20, 2019    (NL) .................................. 2024545

(51) Int. Cl.
*A61B 5/00*    (2006.01)
*A61B 34/20*    (2016.01)
(Continued)

(52) U.S. Cl.
CPC .............. *A61B 34/20* (2016.02); *A61B 5/062* (2013.01); *A61B 5/742* (2013.01); *A61B 5/7405* (2013.01);
(Continued)

(58) Field of Classification Search
CPC ............ A61B 5/06; A61B 5/062; A61B 5/064
See application file for complete search history.

(56) References Cited

U.S. PATENT DOCUMENTS

| 6,129,668 A | 10/2000 | Hynor et al. |
| 7,561,051 B1 | 7/2009 | Kynor et al. |
| 2016/0051164 A1 | 2/2016 | Derichs et al. |

FOREIGN PATENT DOCUMENTS

| EP | 3517068 A1 | 7/2021 |
| WO | 2018045465 A1 | 3/2018 |

OTHER PUBLICATIONS

International search report for PCT/IB2020/062259 dated Apr. 20, 2021.

*Primary Examiner* — Rajeev P Siripurapu
(74) *Attorney, Agent, or Firm* — The Roy Gross Law Firm, LLC; Roy Gross

(57) ABSTRACT

During both invasive and non-invasive treatments and therapies, health professionals need to accurately locate areas of interest. Inaccuracies may mean that not all the area is treated, or the treatment is incomplete. Electro-magnetic and RFID (Radio-Frequency Identification) markers have been developed, but these are bulky and prone to failure. For example, any inaccuracy may result in an incomplete resection or removal of the lesion, requiring additional treatments.

A magnetic field probe 100, 101 is provided for determining an angular disposition 180, 190 of an implantable magnetic marker 200, the probe comprising: a first magnetic sensor 110 close to the distal end 160, and a second magnetic sensor 120, closer to a proximal end 165, configured to determine two or more magnetic field vectors of the marker 200; the probe being further configured: to define two or more marker detection zones 170, 171, 172, 173, 174, extending from the distal end 160; to determine the angular disposition (Continued)

180, 190 to the implantable marker 200; and to determine whether the angular disposition 180, 190 substantially coincides with one of the two or more marker detection zones 170, 171, 172, 173, 174, thereby determining that the marker falls within the one marker detection zones.

By defining two or more marker detection zones, and configuring the probe to determine whether the magnetic marker appears to be within the one marker detection zone, a simplified and intuitive decision algorithm is provided for indicating the disposition of the marker relative to the probe.

21 Claims, 8 Drawing Sheets

(51) Int. Cl.
      *A61B 90/00*       (2016.01)
      *A61B 5/06*       (2006.01)

(52) U.S. Cl.
      CPC ...... *A61B 90/39* (2016.02); *A61B 2090/3958* (2016.02); *A61B 2562/0223* (2013.01); *A61B 2562/043* (2013.01)

MAGNETIC FIELD PROBE FOR DETERMINING A DISPOSITION OF AN IMPLANTABLE MARKER USING TWO OR MORE DETECTION ZONES

This application is a Track One Bypass Continuation of PCT Patent Application No. PCT/IB2020/062259 having International filing date of Dec. 20, 2020, which claims the benefit of priority of Netherlands Patent Application No. 2024545, filed Dec. 20, 2019, the contents of which are all incorporated herein by reference in their entirety.

FIELD

The present disclosure relates to a magnetic field probe for determining an angular disposition of an implantable marker, a detection unit comprising the probe and a method of detecting an angular disposition of an implantable marker.

BACKGROUND

During both invasive and non-invasive treatments and therapies, it is important that health professional be able to accurately locate areas of interest. Frequently, professionals rely on sight and manual manipulation to find and remember areas of interest, often marking an outer surface of skin. In practice, imaging equipment such as X-ray and/or ultrasound, may also be used to assist in the location—however, this relies on being able to distinguish the area of interest from the surrounding tissue using the imaging technologies. Inaccuracies in being able to locate the areas of interest may mean that not all the area is treated, or the treatment is incomplete. This is a problem for both therapeutic and cosmetic procedures and treatments, including removal of tumors, removal of polyps, cosmetic surgery, removal and/or correction of tissues, localization of implanted devices—for example, birth-control devices such as Implanon, may need to be localized.

For example, if lesion resection or removal is prescribed following cancer screening, the surgeon needs to know the location and extent of the lesion. The current golden standard in clinical practice requires the placement of metal anchor wires in the target immediately before the surgical procedure, which risks infection and movement of the wires. Newer solutions use radio-active markers, but the use of radio-active materials is tightly controlled and regulated. Electro-magnetic and RFID (Radio-Frequency Identification) markers have been developed, but these are bulky and prone to failure. Any inaccuracy in locating the area of interest may result in an incomplete resection or removal of the lesion, requiring additional treatments.

In addition, improvements in screening procedures means that smaller and early-stage lesions are increasingly being identified in patients—although this early detection is more beneficial to the patient, small lesions may be difficult for the surgeon to identify and locate. They are also likely to be impalpable. Intra-operative imaging is often cumbersome and expensive.

Recently, the use of implantable magnetic markers (seeds) has been proposed. These provide a higher degree of safety compared to radio-active markers, but still require considerable effort by the healthcare professional to detect the disposition (localization) of the marker. This becomes even more difficult when very small magnetic markers are used to mark very small areas of interest.

U.S. Pat. No. 7,561,051 describes an apparatus for locating a magnet and/or determining the orientation of the apparatus relative to the magnet. In one embodiment, the apparatus includes a multi-axis magnetic field sensor movable in a reciprocating manner so as to permit sensor readings at multiple spaced locations. In another embodiment, the apparatus includes a plurality of multi-axis magnetic field sensors arrayed along a straight line. The apparatus may be used in a number of medical and other applications, including tissue resection, tracking movement of a medical device in a body cavity and tracking movement of an internal organ.

PCT application WO 2018/045465 A1 describes systems and methods for marking the location and extent of an anatomical region-of-interest, such as a tumor, using magnetic seeds whose position and orientation are measured or otherwise detected using a detection device that includes two or more magnetic sensors are described. One or more magnetic seeds are implanted to mark and define the center and extent of an anatomical region-of-interest and a magnetic sensor-based detector system is used to accurately identify the location of the magnetic seeds.

US patent application US 2016/0051164 A1 describes a probe including a first sensor having a first magnetometer and a first accelerometer and a second sensor having a second magnetometer and a second accelerometer is configured for determining the distance and direction to a marker. The marker may be magnetic and may be surgically inserted into a patient's body to mark a specific location. The probe may be used to locate the marker, thus identifying the location. The probe may include a microprocessor that receives an output from the first sensor and an output from the second sensor and determines the distance and direction to the marker.

U.S. Pat. No. 6,129,668 describes a device to detect the location of a magnet coupled to an indwelling medical device within a patient uses three or more sets of magnetic sensors each having sensor elements arranged in a known fashion. Each sensor element senses the magnetic field strength generated by the magnet and provides data indicative of the direction of the magnet in a three-dimensional Space. An initial estimate of the location and orientation of the magnet results in the generation of predicted magnetic field values. Based on the difference between the predicted values and the measured values, the device estimates a new location of the magnet and calculates new predicted magnetic field strength values. This iteration process continues until the predicted values match the measured values within a desired degree of tolerance. A two-dimensional display provides an indication of the location of the magnet with respect to the housing of the detector. A depth indicator portion of the display can be used to provide relative or absolute indication of the depth of the magnet In order to optimally support the surgeon, it is important to provide both distance and direction to the marked location. It is an object of the invention to provide improved directionality detection for magnetic markers or induced magnetic beacons.

General Statements

According to a first aspect of the present disclosure, there is provided a magnetic field probe for determining an angular disposition of an implantable marker, the marker being configured to generate, in use, a magnetic field, the probe comprising: a distal end; a first magnetic sensor close to the distal end; a second magnetic sensor, disposed between the first magnetic sensor and a proximal end, the first and second magnetic sensors being configured and arranged to determine, in use, one or more magnetic field vectors of the marker; the probe being further configured: to define two or more marker detection zones, extending from the distal end along a probe longitudinal axis; to determine the angular disposition to the implantable marker using the one or more magnetic field vectors; and to determine whether the angular disposition substantially coincides with one of the two or more marker detection zones, thereby determining that the marker falls within the one of the two or more marker detection zones.

By defining two or more marker detection zones, and configuring the probe to determine whether the magnetic marker appears to be within one of these two or more marker detection zones, a simplified decision algorithm is provided for indicating the disposition of the marker relative to the probe. For example, a probability may be determined that the marker is within one of the two or more marker detection zones. Alternatively, it is determined whether the angular disposition substantially coincides with the first or second marker detection zone.

In addition, it becomes possible to modify the searching parameters in a way that is intuitive to the user by modifying one or more parameters or aspects associated with the two or more detection zones, such as, for example, an extent, a shape, an orientation, a disposition, a scaling, a resolution, an angular boundary, a longitudinal extent, a transverse extent, and any combination thereof. In other words, the zone is configured to act as a software-controlled collimator. A further advantage over prior art probes is that it is not required to continuously move the probe to determine angular dispositions of the magnetic marker.

It may be advantageous to configure and arrange the probe such that the two or more marker detection zones are substantially symmetrical about the longitudinal axis.

Users may find this particularly intuitive as it allows the probe to be used as hand-held wand, with a detection zone that is not significantly affected by rotating the wand probe around its longitudinal axis.

Configurations that may increase the intuitiveness of use may include further configuring and arranging the probe: to determine an angular disposition of the marker with respect to the distal end of the probe; to determine an angular disposition of the marker with respect to the longitudinal axis of the probe; to determine a longitudinal and/or transverse disposition of the marker with respect to the distal end of the probe; or any combination thereof.

It may be advantageous to configure and arrange the two or more marker detection zones to have a substantially circular, oval, elliptical, triangular, rectangular, or square longitudinal cross-section substantially perpendicular to the probe longitudinal axis. For example, if the probe longitudinal axis extends along the Y axis, the longitudinal cross-section may be determined in an X-Y plane or Y-Z plane.

Additionally or alternatively, the two or more zones may be configured and arranged to have a substantially arc, segment, cylindrical or cone shape. Additionally or alternatively, the two or more zones may be configured and arranged to have a parabolic, linear or hyperbolic shape.

By providing two or more software-configurable detection zones, a user may choose a configuration particularly suited to, for example, the expected location of the marker in the human or animal body, the expected proximity, the expected magnetic field strength, and the expected marker orientation. The user may also select a configuration that they have personally found to be particular efficient for marker localization. As the two or more detection zones may be configured in several dimensions, two or more of these shapes and cross-sectional shapes may be combined. Simple shapes may be used and/or complex shapes.

The two or more marker detection zones may also be configured and arranged to adopt a certain configuration, depending on the expected (by the user) proximity and/or orientation to the marker. This may also be automated to a degree, depending on the measured and/or estimated proximity and/or orientation (by the probe). Any combination in different degrees is also possible.

Additionally or alternatively, the two or more marker detection zones may differ by a parameter selected from the group comprising of: an extent, a shape, an orientation, a disposition, a scaling, a resolution, an angular boundary, a longitudinal extent, a transverse extent, or any combination thereof. Additionally or alternatively, the two or more marker detection zones: share one or more boundaries, are contiguous along one or more axes, are non-contiguous along one or more axes, or any combination thereof.

A further advantage of providing a software-configurable detection zone is that a user may configure and arrange two or more marker detection zones. This may provide, for example, a coarse/fine marker detection zone configuration—as the distal end of the probe gets closer to the magnetic marker, a marker detection zone with a smaller angle may further increase the accuracy and sensitivity.

According to another aspect of the current disclosure, the probe is further configured: to define a further marker detection zone, extending from the distal end along a probe longitudinal axis; and to determine whether the angular disposition substantially coincides with one of the three or more marker detection zones, thereby determining that the marker falls within the one of the three or more marker detection zones.

Another advantage of providing a software-configurable detection zone is that a user may configure and arrange any number of marker detection zones.

Alternatively, wherein the probe is further configured: to define a further marker detection zone, extending from the distal end along a probe longitudinal axis; and to determine whether the angular disposition substantially coincides with: the further marker detection zone; both the first and further marker detection zones; both the second and further marker detection zones; neither the first or further marker detection zones; neither the second or further marker detection zones; or any combination thereof.

Another advantage of providing a software-configurable detection zone is that a user may configure and arrange additional marker detections zones with different degrees of special overlap. These may be substantially fixed, dynamic or any combination thereof.

According to another aspect of the current disclosure, the probe may comprise a plurality of magnetic sensors comprised in one or more 1D, 2D, or 3D arrays.

This allows the concentration of magnetic sensors (or packing density) to be increased. These additional magnetic sensors may be configured and arranged to increase parameters such as, for example sensitivity, accuracy, and reliability. In general, increasing sensitivity at a distal end may make the probe even more intuitive to use.

According to yet another aspect of the current disclosure, the probe may further comprise one or more compensation sensors for measuring a background magnetic field; wherein: the determination, in use, of one or more angular dispositions of the marker further considers the background magnetic field.

Advantageously, an existing sensor or a dedicated sensor may be configured to measure (or detect) a background magnetic field, such as the Earth's magnetic field. The disposition determination may be compensated using background measurements to further increase the accuracy and sensitivity.

According to yet another aspect of this disclosure, wherein the probe is configured and arranged to determine the angular disposition to a magnetic dipole and/or induced magnetic dipole comprised in the marker.

By providing software-configurable detection zones, a user may choose a configuration particularly suited to, for example, the expected magnetic field strength, and the expected marker orientation.

According to a further aspect of this disclosure, the probe is further configured and arranged to provide audio feedback, and an audio characteristic is dependent on a degree of proximity to the marker. Additionally or alternatively, an audio characteristic is different depending on whether the angular disposition substantially coincides with the first or second marker detection zone. Optionally, the audio characteristic is a pitch, a volume, a loudness, an amplitude, a spatial location, a duration, a duration of a pause, a tone, a beep, a pause duration between beeps, a frequency, a frequency spectrum, or any combination thereof.

It may be advantageous if the probe is further configured and arranged to provide a coarse and a fine marker detection zone. It may also be advantageous if the probe is further configured and arranged to select the marker detection zone with a smaller angle as the distal end of the probe gets closer to the marker.

According to another aspect of this disclosure, the probe is configured and arranged to determine one or more aspect of the two or more detection zones based on: one or more measurements from one or more sensors; one or more suitable parameters; one or more parameters provided by a user; selection by a user; or any combination thereof.

Software-configurable detection zones provide a high degree of flexibility in configuration.

According to a still further aspect of the current disclosure, a detector unit may be provided for detecting the angular disposition of an implantable marker, the detector unit comprising the magnetic probe according to the current disclosure.

Optionally, the detector unit further comprises a display, the detector being configured and arranged to indicate to the user the results of the determination on the display. Optionally, the detector unit is further configured and arranged to indicate the first and second marker detection zones on the display According to another aspect of the current disclosure, a method is provided for determining an angular disposition of an implantable marker, the marker being configured to generate, in use, a magnetic field, the method comprising:
  providing a probe comprising a distal end, the probe further comprising: a first magnetic sensor close to the distal end; a second magnetic sensor, disposed between the first magnetic sensor and a proximal end, the first and second magnetic sensors being configured and arranged to determine, in use, one or more magnetic field vectors of the marker;
  configuring and arranging the probe to define two or more marker detection zones, extending from the distal end along a probe longitudinal axis;
  determining the angular disposition to the implantable marker using the one or more magnetic field vectors; and
  determining whether the angular disposition substantially coincides with one of the two or more marker detection zones.

Optionally, the method further comprises: determining whether the angular disposition substantially coincides with the first or second marker detection zone.

Additionally or alternatively, the method comprises: configuring and arranging the probe for an expected location of the marker in the human or animal body, an expected proximity, an expected magnetic field strength, or an expected marker orientation.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments, and which are not necessarily drawn to scale, wherein.

DETAILED DESCRIPTION

In the following detailed description, numerous non-limiting specific details are given to assist in understanding this disclosure. It will be obvious to a person skilled in the art that the computer processing part of the method may be implemented on any type of standalone system or client-server compatible system containing any type of client, network, server, and database elements.

Figure 1A:
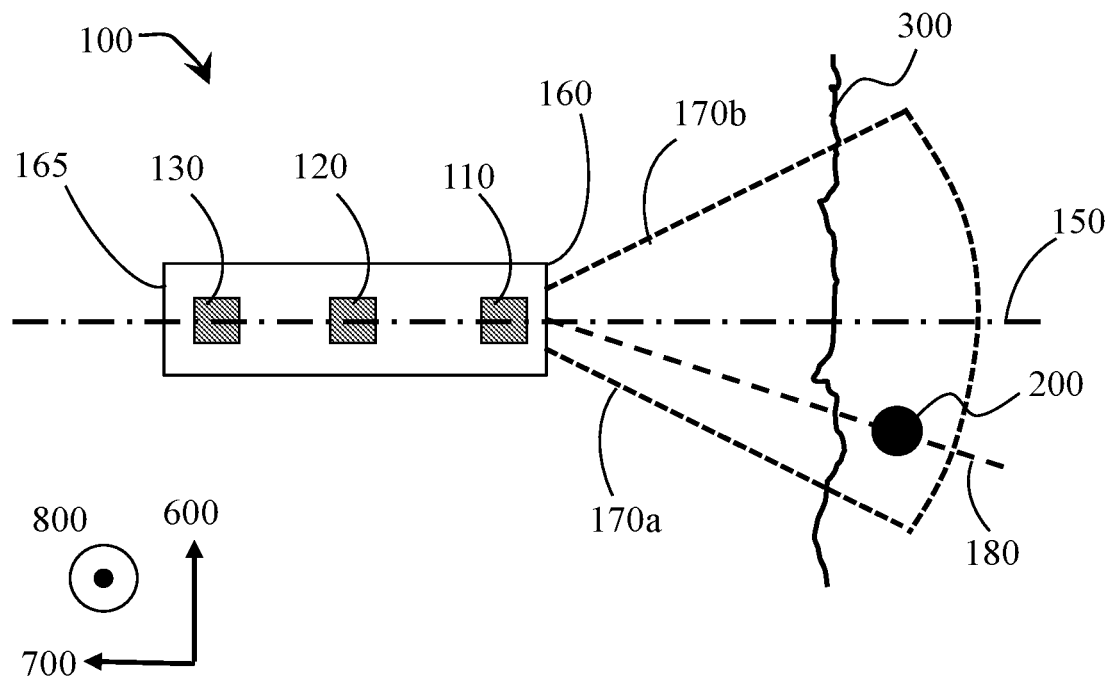
FIGS. 1A and 1B depict longitudinal cross-sections through an embodiment of a magnetic field probe according to the invention.

FIG. 1A depicts a longitudinal cross-section through a magnetic field probe 100 for detecting a disposition (localization) of an implantable marker 200. As depicted, the magnetic marker 200 is implanted below an outer surface of skin 300 to mark an area of interest—this may be a few millimeters or a few centimeters below the outer surface of the skin. This may also be called depth. The marker 200 is configured to generate, in use, a magnetic field—it may comprise, for example, a magnetic dipole.

The marker may be implanted in any convenient way, such as by injection. The injection may be, for example, into soft tissue or organs, or delivery via a bronchoscope to lung bronchii, or coloscope to colon. The method of implantation may depend on, for example, the depth required, the subsequent procedure to be performed, the size of the area of interest, the location of the area of interest, the type of tissue in the area, and the type of tissue surrounding the area. It may be implanted immediately before detection, or some time earlier.

Typically, a suitable marker 200 comprising a magnetic dipole is approximately cylindrical with:
- a diameter of 1.45 mm, a length of 2.19 mm and a remnant field (Br) of 1.43 T (Neodymium N52), or
- a diameter of 1.75 mm, a length of 5 mm and a remnant field (Br) of 1.43 T (Neodymium N52).

A marker with a diameter of 1.45 mm and a length of 4.7 mm may also be suitable.

As higher grades of neodymium become available, they may also be advantageously used with the embodiments of this invention.

Additionally or alternatively, the marker 200 may comprise an induced magnetic dipole. As the magnetic field probe 100 determines the angular dispositions of the marker 200 based on the property of dipole fields, the configuration and arrangement of the marker 200 to produce such a field are less important. Combinations of techniques may also be used to generate a plurality of magnetic dipoles. In the context of this disclosure, an angular disposition may be considered to be the same as an angular arrangement—it is an angular component in the relative position of the marker 200 relative to the probe.

The probe 100 comprises a distal end 160. The magnetic field probe may extend along a probe longitudinal axis 150. To make it easier to compare the different views of the same and different embodiments, axes have also been defined—the plane of the drawing (the paper) is in X 600 and Y 700, substantially perpendicular to each other. The X axis 600 runs from bottom to top and the Y axis 700 runs from right to left. The Z axis 800 is substantially perpendicular to X 600 and Y 700 and exits the plane of the drawing (out of the paper). The longitudinal axis 150 is depicted here as being substantially parallel to the Y axis 700.

The probe 100 is further configured and arranged to determine an angular disposition between a probe reference and the marker 200, as described below—this angular disposition may comprise an angular disposition 180 in XY (depicted in FIG. 1A), an angular disposition 190 (depicted in FIG. 1B) in YZ, an angular disposition (not depicted in FIG. 1A or 1B) in XZ, and any combination thereof. The probe reference may be one or more points of the probe 100 along the longitudinal axis 150, a distal end 160, a proximal end 165 or any combination thereof.

Figure 1B:
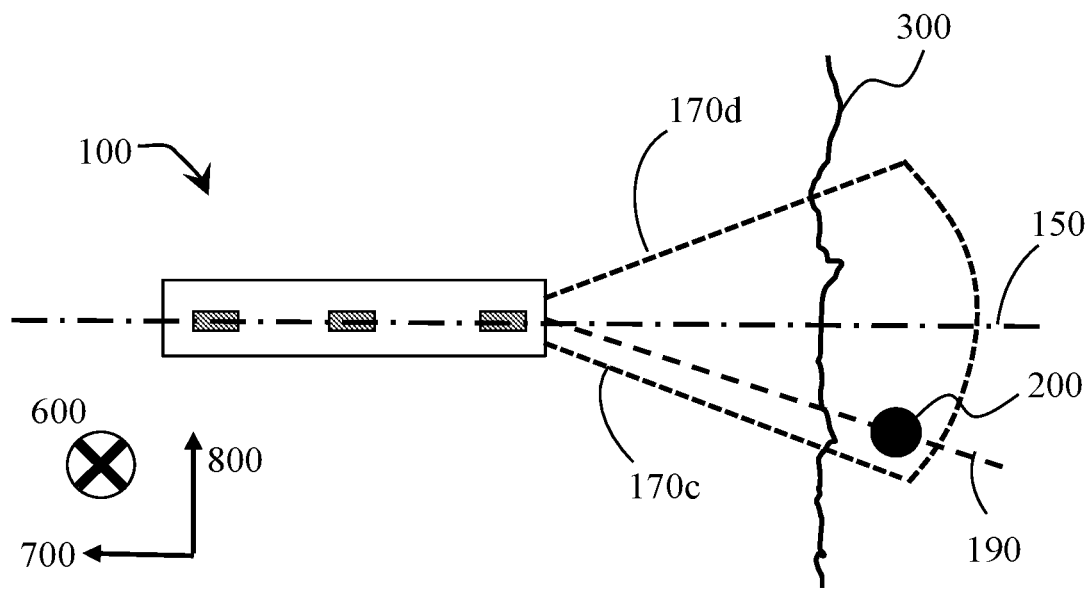

FIG. 1B depicts a further longitudinal cross-section through the magnetic field probe 100 for detecting a disposition (localizing) of the implantable marker 200. The plane of the drawing (the paper) is in Y 700 and Z 800, substantially perpendicular to each other. The Z axis 800 runs from bottom to top and the Y axis 700 runs from right to left. The X axis 600 is substantially perpendicular to Z 800 and Y 700 and enters the plane of the drawing (into the paper). The longitudinal axis 150 is also depicted here as being substantially parallel to the Y axis 700. The probe 100 is further configured and arranged to determine an angular disposition between a probe reference and the marker 200, which may include an YZ angular disposition 190, as described below.

In this example, the distal end 160 is configured and arranged to be disposed close to an outer surface of skin (300).

Additionally or alternatively, the distal end 160 may be configured and arranged to:
- contact an outer surface of skin (300);
- be inserted through an outer surface of skin (300);
- be inserted into a body cavity; or
- any combination thereof.

A user may be particularly interested in being provided with an indication of an angular disposition between the probe longitudinal axis 150 at a distal end 160 and the marker 200. This is particularly advantageous when the probe 100 is configured and arranged to be hand-held by being extended along the longitudinal axis 150, providing an intuitive configuration to determine the direction of the marker 200 relative to a distal end 160 or tip.

The angular dispositions 180, 190 of the marker 200 may be defined and/or expressed in any convenient parameter, such as degrees or radians.

The probe 100 comprises at least a first magnetic sensor 110 and a second magnetic sensor 120, configured to measure at least the vector of the local magnetic field (Bx, By, Bz) generated by the marker 200. These properties are used to determine one or more angular dispositions 180, 190 using a software algorithm.

The distal end 160 may be disposed at a distance from the outer surface of skin 300—a spacer may be used to maintain a fixed distance, or the distance may be zero if the probe 100 is further configured and arranged to contact the outer surface of skin 300. The probe 100 may be further configured and arranged to be pushed against the outer surface of skin 300 to create an indent which may further reduce the distance between the distal end 160 of the probe 100 and the marker 200. In general, the smaller the distance between the probe 100 and the marker, the greater the amplitude of any signal measured. For some treatments, the probe 100 may further configured and arranged to be inserted through the outer surface of skin 300 and/or into a body cavity to further reduce the distance between probe 100 and marker 200. This may be, for example, via a surgical incision or via a natural orifice.

The probe 100 may be comprised in a detection unit or device (not shown). It will be clear to the skilled person that functionalities for determining the one or more dispositions may be implemented in the hardware and software of the magnetic probe 100, or they be implemented in the hardware and software of the rest of the detector. The functionalities may also be divided in any convenient way between the magnetic probe 100 and the rest of the detector unit.

A detection unit or device for a probe 100 may comprise one or more of the following:
- an optional electrical and/or mechanical connection, configured to attach to a proximal end 165 of the probe 100. It may be advantageous to make the attachment releasable. The connection may also be wireless, configured and arranged to allow at least data transmission between the probe 100 and the rest of the detector;
- a power supply to provide energy to the probe magnetic sensors;
- a processor, configured to collect magnetic sensor measurement values, and to determine one or more angular dispositions 180, 190 (angular inclinations) using an appropriate software algorithm;
- optionally, a display may also be provided to indicate to the user the results of the determination. Preferably, one or more angular dispositions 180, 190 to the marker 200 are displayed graphically. Additionally or alternatively, one or more detection zones (as described below) are indicated, providing intuitive feedback. Additionally or alternatively, numbers may be displayed.

Additionally or alternatively, audio feedback may also be provided—this is described in more detail below. The distances (dispositions) may be displayed, for example, as relative values and/or absolute values. Audio feedback may be provided, for example, similar to the way distance to an object is indicated with an automobile parking sensor with different tones.

Other examples of audio characteristics that may be configured to be dependent on a degree of proximity to the marker 200 include a pitch, a volume, a loudness, an amplitude, a spatial location, a duration, a duration of a pause, a tone, a beep, a pause duration between beeps, a frequency, a frequency spectrum, or any combination thereof.

If the probe is configured to define two or more detection zones, the indication and/or audio feedback may be different depending on whether the angular disposition (180, 190) substantially coincides with:
 a first marker detection zone;
 a second marker detection zone;
 both the first and second detection zones;
 neither the first or second detection zones; or
 any combination thereof.

The probe 100 comprises two or more magnetic sensors:
 110: a first magnetic sensor, close to the distal end 160 of the probe 100; and
 120: a second magnetic sensor, disposed between the first magnetic sensor 110 and a proximal end 165 of the probe 100. In other words, further away from the distal end 160 than the first magnetic sensor 110.

The sensors 110, 120 are configured and arranged to determine, in use, one or more B-field 3D vector measurements of the marker's 200 magnetic field. Typically, the sensor output is a 3D vector of a B-field—with two or more sensors, an angular disposition may be derived.

First and second measurements, associated with the first 110 and second 120 sensor, are used in a software algorithm to determine one or more angular dispositions 180, 190 of the marker 200. An angular disposition 180, 190 is a measurement (or estimation) of a direction to the marker 200 associated with the probe 100 as a whole.

Optionally, the probe may comprise at a third magnetic sensor 130. This is advantageously closer to the proximal end 165 of the probe 100 than the first 110 and second 120 magnetic sensors (in other words, further away from the distal end 160). It may be configured and arranged as a compensation sensor to detect a background magnetic field, such as a naturally-occurring magnetic field (from the Earth), a man-made field present due to equipment being operated in the environment where the measurements and determinations are performed, and/or a diamagnetic field created by the tissue in or around the area of interest.

Additionally or alternatively, magnetic sensors 110. 120 such as 3-axis Hall sensors which measure three field components Bx, By and Bz using 3 magnetic detectors—typically such a Hall-sensor package is an IC comprising three (3D) substantially mutually perpendicular detectors, providing measurement of three degrees of freedom at approximately the same physical position in the probe. The sensors 110, 120 may be the same type or different types.

In this disclosure, a sensor and detector are sometimes used interchangeably. In general, a sensor is a single encapsulated package comprising one or more detectors. A sensor with a single magnetic detector may be considered a sensor or a detector.

If a sensor package comprises two detectors with a physical separation between the detectors sufficiently large to measure substantially different values for a particular B-vector of the marker's 200 magnetic field, then in the terms of this disclosure, such a package comprises two sensors—each of the detectors provides a B-vector measurement of the marker's 200 magnetic field relating to substantially different sensor positions (or dispositions) within the probe 100. If the physical separation between the detectors is too small (they measure substantially the same value for a particular B-vector), then in the terms of this disclosure, such a package comprises one sensor—each of the detectors provides a vector measurement of the marker 200 relating to substantially the same position (or disposition) within the probe 100.

Note that in some packages, two or more detectors may be configured to measure different orientations—for example, some Hall sensor packages comprise three detectors, oriented substantially perpendicular to each other. They are considered as being comprised in the same (one) sensor as they measure B-vectors associated with substantially the same position (or disposition).

As depicted in FIG. 1A, a 1D array of at least two magnetic sensors 110, 120 may be used. The sensors 110, 120 are depicted disposed along the longitudinal axis 150 of the probe 100—this is not essential as their relative positions (dispositions) may be determined from measurement and/or design data and taken into account (considered) in the software algorithm. The probe 100 is configured and arranged to convert the B-vector measurements from the sensors 110, 120 to any probe 100 reference plane or reference axis. It is particularly advantageous to dispose the sensors 110, 120 along the longitudinal axis 150 and to use this longitudinal axis 150 as a reference for the angular measurements as this simplifies the geometric conversion of measurement data.

These magnetic detectors 110, 120 may be any suitable type, such as magnetometers, flux gate sensors, geomagnetic sensors, Lorentz force digital MEMS, magneto-inductive sensors, magneto-resistive sensors, Hall sensors, magnetic tunnel junctions and any combination thereof. Many IC packages are available which are small and contain 3 axis detection. So a 'many-axis' solution may be provided with simple PCB design and preferably a smaller probe diameter. The sensor packages proposed below are examples. They are digital and therefore relatively straightforward to interface as less analog design is required.

TI DRV425 Flux Gate sensor (1D)
Technology: Flux gate
Size: 4×4×0.8 mm
Range: +/−2 mT (single axis)
Resolution: (analog, depends on ADC)
RMS noise: 0.42 uT @ 1000 Hz (0.2 uT @ 50 Hz)
Offset: 8.3 uT, +1.4 uT hysteresis+0.4 temperature drift
Gain error: 0.3%
Abs Max Field: >2T in any direction
Note: The offset may be reduced by using a correction sensor with a good zero-field offset performance. Another type of sensor, for example, may be integrated in the probe 100 provide a degree of offset and/or drift correction for the fluxgates. Preferably, such a correction sensor is located close to, or at, the proximal end to reduce the influence of a magnetic field property of the magnetic marker 200.

Bosch BMM150 3-axis digital geomagnetic sensor (3D)
Technology: FlipCore
Size: 1.56×1.56×0.6 mm
Range: +/−1.2 mT (x,y); +/−2 mT (z)
Resolution: 0.3 uT (LSB)
RMS noise: 0.3 uT @ 20 samples/s
Offset: 40 uT without Software compensation, 2 uT after compensation (typical)
Gain error: 5% (after compensation)
Abs Max Field: >7T in any direction
ST LIS3MDL (1D)
Technology: Lorentz force digital MEMS
Size: 2×2×1 mm
Range: +/−1.6 mT (x,y,z) (user selectable 0.4, 0.8, 1.2 mT)
Resolution: 0.015 uT (LSB) (@0.4 mT range; 0.06 uT @ 1.6 mT range)
RMS noise: 0.3 uT(x,y); 0.4 uT(z) @ 1.2 mT range
Offset: 100 uT; drifts when fields >5 mT applied
Gain error: 0.15% Full Scale (best fit straight-line non-linearity)
Abs Max Field: <0.1 T in any direction
ST IIS2MDC (3D)
Technology: 3-axis digital output magnetometer high-accuracy, ultra-low power
Noise: 0.3 uT with low-pass filter or offset cancellation enabled. 1SD at 20 samples per second.
Offset error: 6 uT; correctable to 1.2 uT over 20 degr. C range. Hysteresis measured at 3 T was 53 uT and 13 uT with a 5 mT field.
Offset change: with temperature 0.03 uT per degrees C.
Gain error: 1.5% (typical), 7% (max)
Gain change: with temperature 0.03% per degrees C.
Melexis MLX90393 Micropower Triaxis Magnetometer (3D)
Technology: Hall
Size: 3×3×1 mm
Range: +/−5-50 mT (x,y,z) (user selectable)
Resolution: 0.16 uT(x,y); 0.3 uT(z) (LSB)
RMS noise: 0.7 uT(x,y); 0.9 uT(z) @ 50 Sample/s
Offset: 0 uT 2.7 uT/C temperature drift (on-chip compensation available)
Gain error: <1% cross axis sensitivity+3% over temperature
Abs Max Field: —
MEMSIC MMC3416xPJ (3D)
Technology: AMR
Size: 1.6×1.6×0.6 mm
Range: +/−1.6 mT (x,y,z) (user selectable 0.4, 0.8, 1.2 mT)
Resolution: 0.015 uT (LSB) (@0.4 mT range; 0.06 uT @ 1.6 mT range)
RMS noise: 0.15 uT @ 125 samples/s
Offset: Repeatability Error 0.1% Full scale=1.6 uT
Gain error: —
Abs Max Field: 1 T
AKM AK09970N (3D)
Technology: HALL
Size: 3×3×0.6 mm
Range: +/−36 mT (x,y); +/−102 mT (z)
Resolution: 1.1 uT (LSB)
RMS noise: 5 uT @ 100 samples/s
Offset: 743 uT (x,y), 1050 uT (z)
Gain error: 10%
Abs Max Field: —
PNI RM3100 sensor system (3D)
Technology: Magneto-inductive
Size: 15.24×12.8×3×10.5 mm
Range: +/−800 uT(z)
Resolution: 13 nT (LSB)
RMS noise: 15 nT @ 100 samples/s
Offset: Repeatability 8 nT hysteresis 15 nT
Gain error: linearity 0.5%
Abs Max Field: —
Note: Sensor system contains 3 coils and a driver IC with digital interface Longitudinal sensor array lengths 400 of 40 mm to 50 mm are preferred.

Each sensor 110, 120 measures respectively the B-field 3D vector of any local magnetic field, which may comprise any background magnetic field, such as the Earth's magnetic field, and the magnetic field of the marker 200. These measurements are provided to a software algorithm which combines them, together with physical parameters such as orientation, sensitivity, sensor separation distance, to determine an angular disposition 180, 190 of the magnetic marker 200 relative to the predetermined reference position of probe 100.

One of the insights upon which the invention is based is that when the inclination (angular disposition) is zero (in other words, when the marker 200 is disposed along the longitudinal axis 150 of the probe 100, for example in the Y-Z plane 700-800), the magnetic fields measured at all the sensors 110, 120 disposed along the longitudinal axis are in substantially the same direction. When this is detected with a hand-held probe 100, the probe 100 will "point" substantially in the direction of the marker 200.

In hand-held applications, the user may rotate the probe 100 to different inclinations, for example in the Y-Z plane 700-800, such that the longitudinal axis 150 has a plurality of orientations with respect to the skin 300. By continuously monitoring the magnetic field vector measurements and determining the degree of deviation (the differences) in field directions measured by each sensor 110, 120, an indication of the relative inclination (angular disposition) to the marker 200 may be provided. When the degree of deviation is below a predetermined threshold, the probe 100 will substantially "point" to the marker 200.

It may be advantageous to configure the probe 100 to reduce noise as much as possible to improve the accuracy of the measurements—for example, by:
using more sensitive sensors 110, 120;
using a marker 200 that provides a stronger magnetic field
by using a larger number of sensors 110, 120;
by using one or more averaging filters;
and any combination thereof.

For a magnetic dipole comprised in the marker 200 at an origin, and with a dipole moment m pointing in the Z-direction 800, the magnetic fields in spherical polar coordinates are given by the equations:

$$B_r = 2|m| \cos \theta / r^3$$

$$B_\theta = |m| \sin \theta / r^3$$

$$B_\varphi = 0 \hspace{3cm} \text{(Equations 1)}$$

Figure 3A:
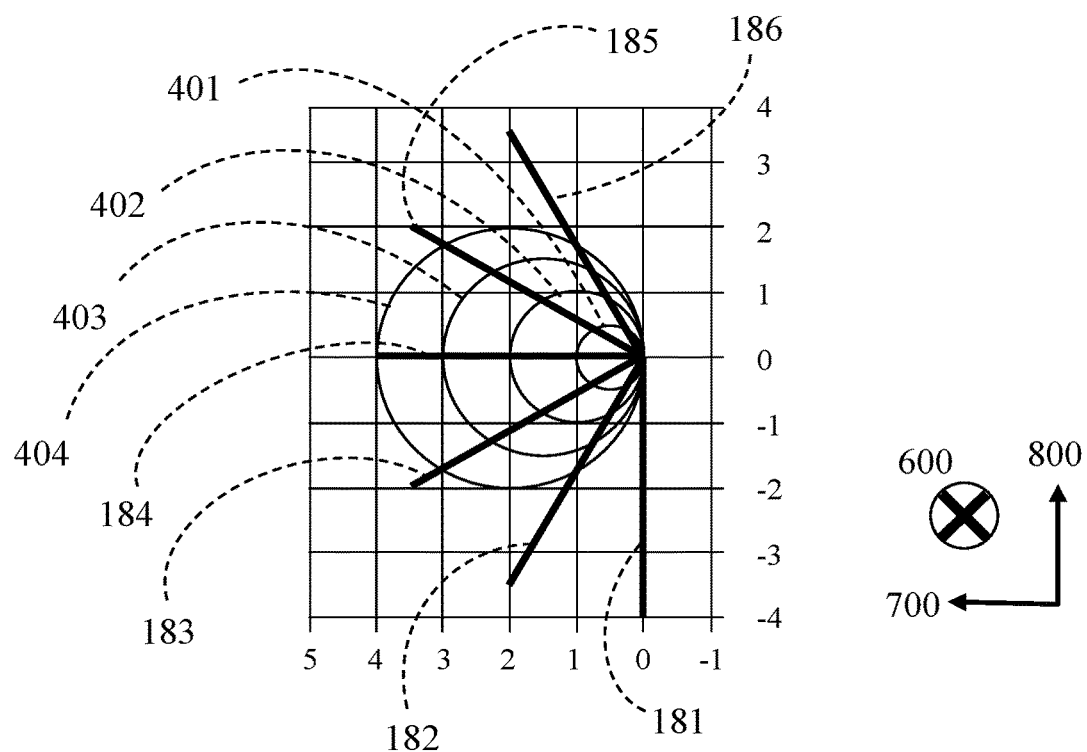
FIG. 3A depicts a simulated schematic diagram of approximately circular field lines that represent cross-sections of a magnetic field, generated by a magnetic dipole.

FIG. 3A depicts a simulated schematic diagram of approximately circular field lines 401, 402, 403, 404 that represent cross-sections in the Y-Z plane 700-800 of a magnetic field, generated by a magnetic dipole 200 at the Y-Z 700-800 origin. The Z-axis 800 represents nominal distance units, from −4 at the bottom to +4 at the top, passing through 0. The Y-axis 700 also represents nominal distance units, from −1 at the right to +5 at the left, passing through 0. The dipole moment m is disposed along the Z-axis 800. The X-axis 600 enters the plane of the drawing (goes into the paper). The field-lines 401, 402, 403, 404 all pass through the Y-Z 700-800 origin 0, 0, depicting field lines that radiate out from the origin:

- the first field line 401 has a nominal diameter of 1 distance units, passing approximately through Y-Z 700-800 co-ordinates 0, 0/0.5, −0.5/1, 0/0.5, 0.5
- the second field line 402 has a nominal diameter of 2 distance units, passing approximately through Y-Z 700-800 co-ordinates 0, 0/1, −1/2, 0/1, 1
- the third field line 403 has a nominal diameter of 3 distance units, passing approximately through X-Y 600-700 co-ordinates 0, 0/1.5, −1.5/3, 0/1.5, 1.5
- the fourth field line 404 has a nominal diameter of 4 distance units, passing approximately through Y-Z 700-800 co-ordinates 0, 0/2, −2/4, 0/2, 2

For clarity, only four field lines are shown—in practice, additional field lines would be present and measurable with suitably sensitive magnetic sensors 110, 120.

Also depicted are six orientations of a probe 100, each representing an inclination 181 to 186—the probe 100 has an extension along the longitudinal axis 150 of four nominal distance units. In each position, the Y-Z angular disposition 190 is approximately 0 degrees because the distal end 160 "points" to the dipole 200, and the deviation between the vector measurements measured by the sensors 110, 120 is very low or approximately zero:

- a first inclination 181, the probe 100 extending from 0, −4 to 0, 0, the distal end 160 coinciding with the Y-Z 700-800 origin 0, 0. The field lines 401, 402, 403, 404 intersect the probe 100 at approximately 0 (or 180) degrees for all sensors 110, 120.
- a second inclination 182, the probe 100 extending from approximately 2, −3.3 to 0, 0, the distal end 160 coinciding with the Y-Z 700-800 origin 0, 0. The field lines 401, 402, 403, 404 intersect the probe 100 at approximately 50 degrees.
- a third inclination 183, the probe 100 extending from approximately 3.4, −2 to 0, 0, the distal end 160 coinciding with the Y-Z 700-800 origin 0, 0. The field lines 401, 402, 403, 404 intersect the probe 100 at approximately 70 degrees.
- a fourth inclination 184, the probe 100 extending from approximately 4, 0 to 0, 0, the distal end 160 coinciding with the Y-Z 700-800 origin 0, 0. The field lines 401, 402, 403, 404 intersect the probe 100 at approximately 90 degrees.
- a fifth inclination 185, the probe 100 extending from approximately 3.4, 2 to 0, 0, the distal end 160 coinciding with the Y-Z 700-800 origin 0, 0. The field lines 401, 402, 403, 404 intersect the probe 100 at approximately 110 degrees.
- a sixth inclination 185, the probe 100 extending from approximately 2, 3.3 to 0, 0, the distal end 160 coinciding with the Y-Z 700-800 origin 0, 0. The field lines 401, 402, 403, 404 intersect the probe 100 at approximately 130 degrees.

So, by exploiting this property of the magnetic field of a magnetic dipole generated by the marker 200, orientations of the probe 100 with approximately zero YZ angular disposition 190 may be determined by orientations where the deviation in field direction measured by the magnetic sensors 110, 120 is very low or approximately zero. Preferably the deviation is less than approximately 15 degrees.

The field lines 401, 402, 403, 404 intersect the magnetic sensors 110, 120 of the probe 100 at the substantially the same angle. The angle of the field lines 401, 402, 403, 404 depends to a high degree on the angle that the probe 100 makes with the magnetic dipole generated by the marker 200. This is because the dipole fields are self-similar, i.e. field lines further from the dipole 200 have substantially the same shape as the field lines closer to the dipole 200.

Figure 3B:
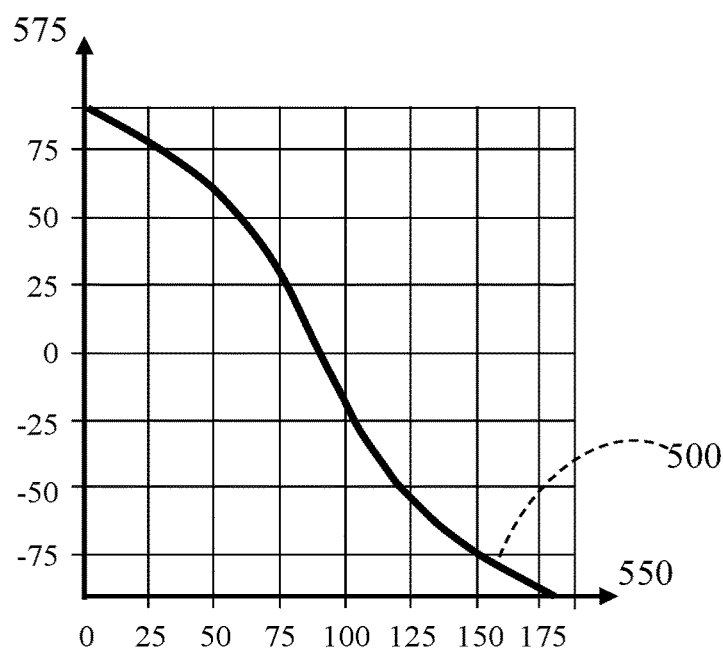
FIG. 3B depicts the relationship between probe inclination and values of the inclination of the fields in the probe plane.

This relationship 500 is depicted in FIG. 3B—along the horizontal axis, values of the probe inclination θ 550 are plotted left to right from 0 to 180 degrees, and along the vertical axis, values of the inclination of the fields in the probe plane 575 are plotted from −90 at the bottom to +90 degrees at the top. The relationship passes through the following points:

| Probe inclination 550 (deg) | Field inclination 575 (deg) | disposition (FIG. 3A) |
|---|---|---|
| 0 | +90 | not depicted |
| 50 | +60 | 186 |
| 70 | +30 | 185 |
| 90 | 0 | 184 |
| 110 | −30 | 183 |
| 130 | −60 | 182 |
| 180 | −90 | 181 |

If the probe 100 is moved to different inclinations with a constant Z 800 disposition, then θ is related to the position of the sensors 110, 120 from the marker 200:

$$\tan(\theta) = Z_{sen}/Y_{sen}$$

$$\tan(\alpha) = \tan(\theta)/2 = (Z_{sen}/Y_{sen})/2$$

Figure 7:
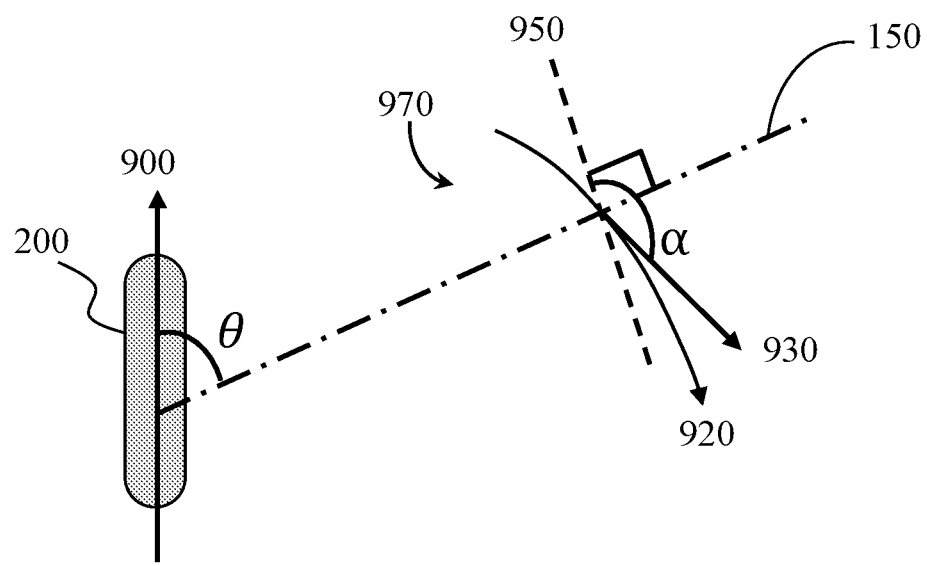
FIG. 7 depicts an example of expected magnetic field components when the probe points directly towards the magnetic dipole.

FIG. 7 depicts the expected magnetic field component when the probe points directly towards the magnetic dipole.

A magnetic marker 200 is longitudinally extended along a marker magnetic axis 900. The marker magnetic axis 900 is the axis of the dipole moment (a vector) of the magnet. It is convenient to use magnetic markers 200 which are substantially aligned with the dipole moment 900, but other shapes and other alignments of markers 200 may also be used.

In the case depicted, the probe longitudinal axis 150 is directed towards the magnetic marker 200 (the probe is pointing towards the center of the magnetic dipole of the magnetic marker 200)—the probe longitudinal axis 150 is intersected with the marker magnetic axis 900 at an inclination θ.

At a detection position 970, having spherical co-ordinates (r, θ, φ or r, theta, phi), a transverse axis 950 is depicted which intersects the probe longitudinal axis 150 substantially perpendicularly. At the detection position 970, a magnetic field (B) 920 created by the magnetic marker 200 is present and detectable. At the detection position 970, a magnetic field vector 930 B is detectable at an angle α (alpha) with the transverse axis 950.

As the probe points directly at the magnetic marker 200 in the case depicted, the component of the magnetic field vector 930 B in the azimuthal direction (Bφ) may be considered to be approximately zero. The angle α (alpha) may be considered to mainly correspond to the inclination θ (theta) of the probe with respect to the magnetic dipole of the magnetic marker 200

So, for determining angular dispositions of the magnetic marker 200, the magnetic field vector 930 B may be considered to have two components:

|B| sin α=Br—along the probe longitudinal axis 150, which is in a radial direction r

|B| cos α=B_θ—along the direction of inclination θ.

In prior art systems, a 1D line of sensors may be used to provide both distance and direction measurements—however, the accuracy may become poor when the probe does not point directly at the magnetic marker 200.

From FIG. 3A and FIG. 3B, the skilled person will realize that when two or more magnetic sensors disposed on 1D line indicate approximately the same magnetic field angle α (alpha), the probe is pointing towards the magnetic marker 200. From the amplitude of the measured fields, the distance to the magnetic dipole 200 may be calculated.

When the multiple sensors indicate different angles α (alpha), the probe is pointing away from the magnetic marker 200. Any artificial measure for the deviation of angles over the various sensors may be used as an indicator of how much the probe points away from the magnetic marker 200.

Figure 4A:
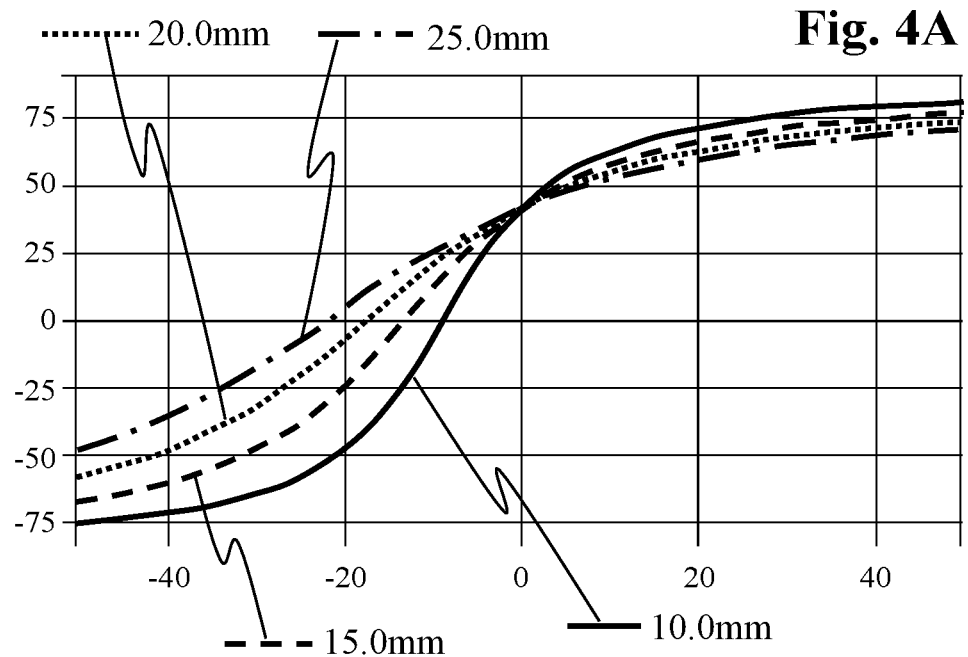
FIGS. 4A and 4B depict measurements made at each magnetic sensor as the probe was scanned through different angular dispositions at a fixed inclination.
Figure 4B:
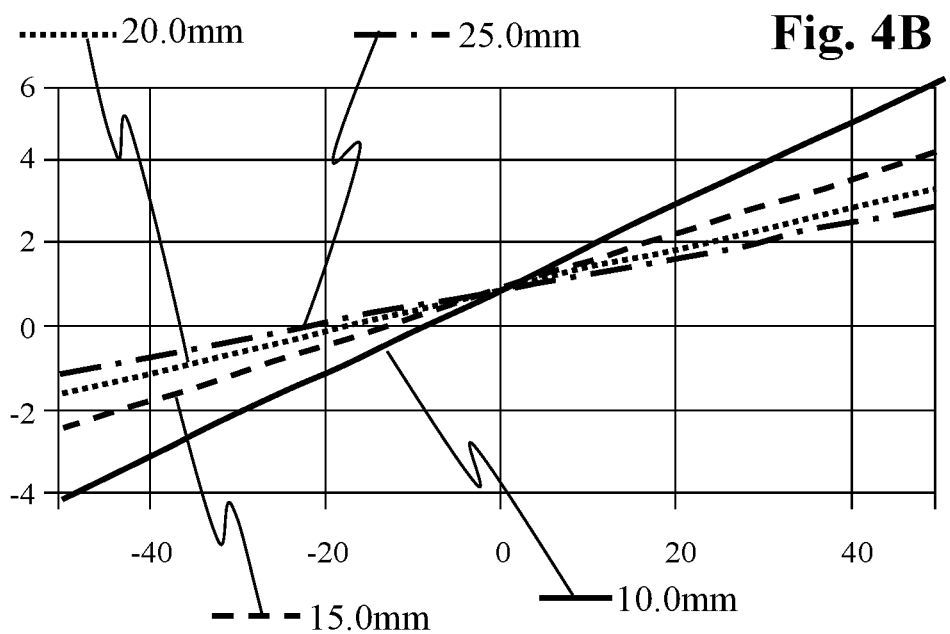

FIGS. 4A and 4B depict measurements made at each magnetic sensor 110, 120 disposed along the longitudinal axis 150 as the probe 100 was scanned through different XY angular dispositions 190 at a fixed inclination θ 191, 192, 193, 194, 195, 196 of 30.0 degrees. By comparing the B-field vector measured with each magnetic sensor 110, 120, the XY angular disposition 190 at which the probe substantially directly "points" at the marker 200 (in other words, when the XY angular distribution 190 is substantially zero) may be determined by identifying the point where the graphs intercept (also called zero intercept or "intercept=0" point).

FIG. 4A depicts the measurement of B-field inclinations at sensors in degrees, the field inclination being plotted on the vertical axis from −75 degrees to +90 degrees and on the horizontal axis in the probe Z 800 disposition from −50 mm to +50 mm. Four graphs are shown, one for each sensor 110, 120 disposed along the longitudinal axis 150 at the following distances, along the Y-axis 700 from the distal end 160—10.0 mm, 15.0 mm, 20.0 mm and 25.0 mm (depicted from bottom to top in that order on the left side of the figure). Each graph forms a flattened S, which passes through the same zero intercept (0 mm on the horizontal axis).

FIG. 4B depicts the same data as in FIG. 4A (four graphs, one for each sensor 110, 120 disposed along the longitudinal axis 150 at the following distances, along the Y-axis 700 from the distal end 160—10.0 mm, 15.0 mm, 20.0 mm and 25.0 mm, depicted from bottom to top in that order on the left side of the figure). FIG. 4B differs from FIG. 4A in that the vertical axis used is the tan of the B-field inclinations from −4 to +6. The advantage of using a tan function is that the characteristics become approximately linear, allowing them to be more easily used to estimate and/or determine the position of the zero intercept (0 mm on the horizontal axis).

Figure 5A:
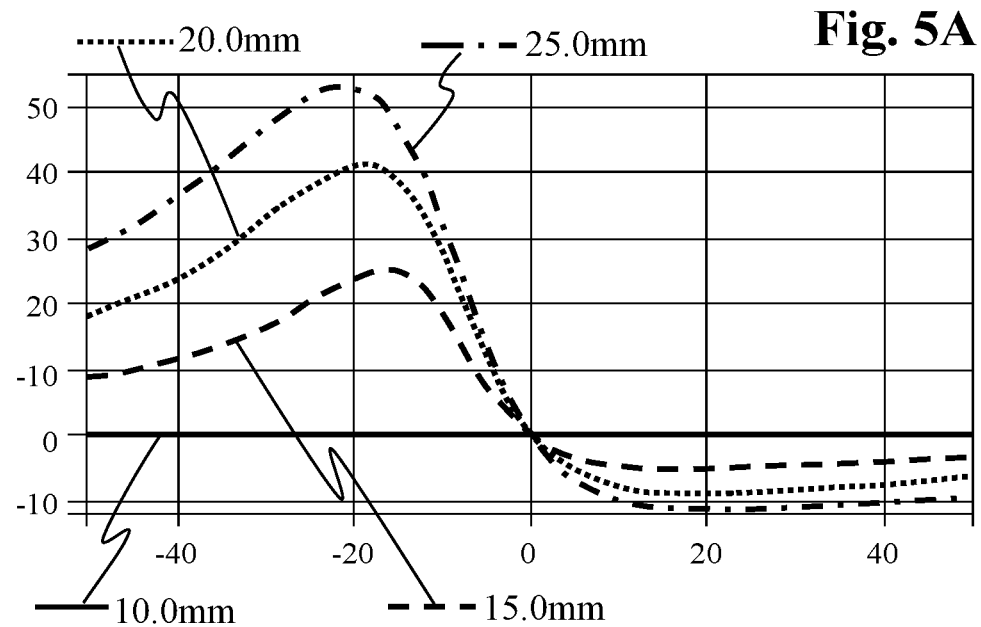
FIGS. 5A and 5B depict differences in B-field inclination, measured at distances 15.0 mm, 20.0 mm and 25.0 mm compared to magnetic sensor closest to distal end, namely the sensor at 10.0 mm.

Similarly, the difference in B-field inclination may be used, comparing the values measured at the 15.0 mm, 20.0 mm and 25.0 mm compared to the magnetic sensor closest to the distal end, namely the sensor at 10.0 mm. These graphs are depicted in FIG. 5A in the order 10.0 mm (reference), 15.0 mm, 20.0 mm and 25.0 mm from bottom to top in that order on the left side of the figure. The difference in B-field inclination with the 10.0 mm values are plotted on the vertical axis, from −12 degrees to +55 degrees. The horizontal axis depicts disposition from −50 mm to +50 mm. As the other values are compared to the 10.0 mm values, the 10.0 mm values are depicted as a horizontal line at the 0 difference line. Again, the graphs intercept each other at the zero intercept (0 mm on the horizontal axis).

Figure 5B:
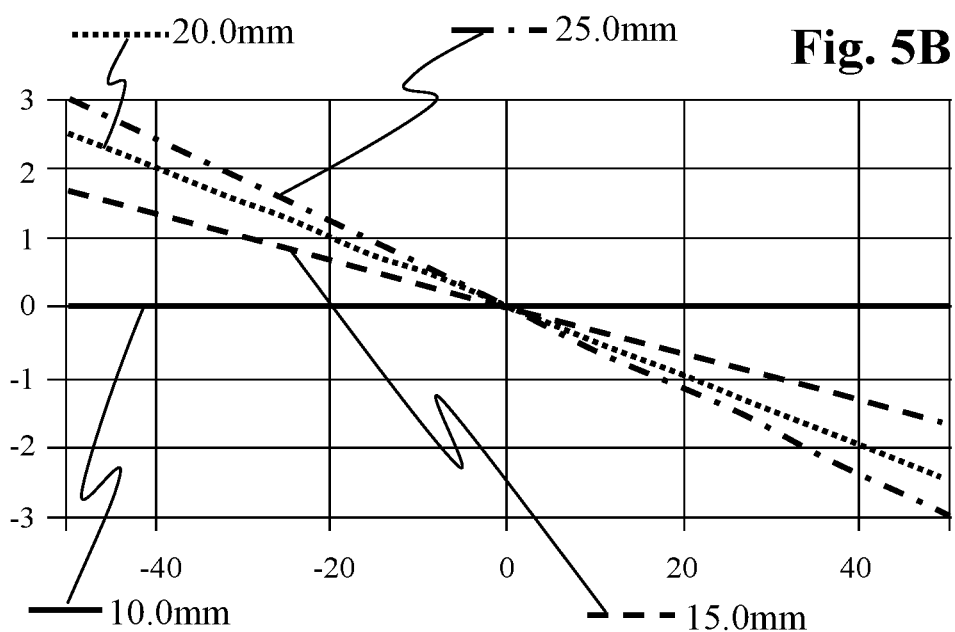

FIG. 5B depicts the same data as in FIG. 5A (in the order 10.0 mm—reference, 15.0 mm, 20.0 mm and 25.0 mm from bottom to top in that order on the left side of the figure). As the other values are compared to the 10.0 mm values, the 10.0 mm values are depicted as a horizontal line at the 0 difference line. FIG. 5B differs from FIG. 5A in that the vertical axis used is the tan of the B-field inclination differences from −3 to +3. The advantage of using a tan function is that the characteristics become approximately linear, allowing them to be more easily used to estimate and/or determine the position of the zero intercept (0 mm on the horizontal axis).

So, the deviation of the B-field inclination angles may be used as a measure of angular disposition to the marker: The probe points directly at the marker when the deviation is a minimum. The deviations may be quantified, using, for example:

Mean of absolute—in other words, the field angles relative to the mean of the fields is monitored. This is the preferred option—the mean of the fields as the reference puts more weight on the stronger fields, which may result in a higher SNR. The field closest to the distal end 160 may also be used, although this may require additional measures to reduce noise.

Mean of the B-field tan depicted in FIG. 4D.

Instead of using the means indicated, an average tangent may be used.

FIG. 1A further depicts a marker detection zone 170a, 170b extending from the distal end 160 along a probe longitudinal axis 150. Although depicted with a triangular cross-section in the XY plane 600-700 and substantially symmetrical, this is not essential—any form of cross-section may be used. The marker detection zone may be mainly determined by two or more angular boundaries 170a, 170b as indicated by the dashed lines. Additionally and optionally, the distance between the two or more angular boundaries 170a, 170b proximate the distal end 160 of the probe 100 may be predetermined and/or controlled. Additionally and optionally, the extent that the marker detection zone extends along the longitudinal axis 150 away from the distal end 160 of the probe 100, depicted as a curved dashed line, may be predetermined or controlled.

Similarly, FIG. 1B depicts further extents of the marker detection zone 170c, 170d, extending from the distal end 160 along a probe longitudinal axis 150. Although depicted with a triangular cross-section in the YZ plane 700-800 and substantially symmetrical, this is not essential—any form of cross-section may be used. The zone may have an extent in XY 600-700 and/or YZ 700-800.

The marker detection zone may be mainly determined by two or more angular boundaries 170c, 170d as indicated by the dashed lines. Additionally and optionally, the distance between the two or more angular boundaries 170c, 170d proximate the distal end 160 of the probe 100 may be predetermined and/or controlled. Additionally and optionally, the extent that the marker detection zone extends along the longitudinal axis 150 away from the distal end 160 of the probe 100, depicted as a curved dashed line, may be predetermined or controlled.

Although the cross-sections depicted in FIGS. 1A and 1B are substantially the same shape, with different extents, this is not essential. For example, the marker detection zone 170a, 170b, 170c, 170d may optionally have a substantially circular, arc, segment, oval, elliptical, triangular, rectangular, or square transverse cross-section substantially perpendicular to the longitudinal axis 150.

If the marker detection zone 170a, 170b, 170c, 170d is substantially symmetrical about the longitudinal axis 150, it may provide a more intuitive probe 100 for finding markers 200, particularly when the probe is configured to be handheld. For example, it may be defined as a cylinder or a cone-shape. A cone-shaped marker detection zone may further have a parabolic, linear or hyperbolic shape.

Parabolic=a wider angle proximate the distal end 160 and a narrower angle remote from the distal end towards a more negative Y 700 disposition Linear=approximately the same angle proximate the distal end 160 and remote the distal end 160 towards a more negative Y 700 disposition. This may also be described as a focused beam.

Hyperbolic=a narrower angle proximate the distal end 160 and a wider angle remote from the distal end towards a more negative Y 700 disposition.

The marker detection zone 170a, 170b, 170c, 170d may be defined using software—for example, during measurement of the B-field vectors, angular dispositions 180, 190 that are estimated/measured as being outside the marker detection zone 170a, 170b, 170c, 170d may be suppressed. In other words, the software may be configured to only consider the vector measurements in the angular disposition calculation if they appear to indicate that the marker 200 falls within the marker detection zone 170a, 170b, 170c, 170d. In other words, the zone is configured to act as a software-controlled collimator. Additionally and optionally, the extent that the marker detection zone extends along the longitudinal axis 150 may also be used to determine whether the marker 200 falls within a longitudinally-limited marker detection zone.

Defining the zone in software, means that simple shapes, such as cylinders, slits and cones may be used. Alternatively or additionally, complex shapes may also be used—for example, a narrow cone close to the distal end 160 of the probe 100, which fans out wider further away from the distal end 160 or defines a straight (cylindrical) beam further away from the distal end 160.

This may be implemented as a straightforward goniometric test, implementing the desired detection volume. If the marker 200 appears to be on the edge of the zone 170a, 170b, 170c, 170d, noise may result in a marker 200 being sometimes suppressed, and sometimes used. Solutions that may be implemented include:

1) Hysteresis for the measurement—for example, once it has been considered to be inside the zone 170a, 170b, 170c, 170d, movement of a considerable distance and/or angle should occur before the B-field vector measurement is suppressed.

2) The 3D localization output, described in an earlier patent application by the same applicant, NL 2022093, may also have a degree of uncertainty. If the position uncertainty is considered to be a heat map in space, it may be multiplied with the zone 170a, 170b, 170c, 170d, followed by integrated over the volume. If the integral is above a threshold, the values are used in the determination of the angular disposition 180, 190.

3) Shaping the weights of the zone 170a, 170b, 170c, 170d to be tapered. For example, the probe 100 may be configured and arranged to evaluate the B-field vectors and returns the Jacobian, which may be used to give an indication of the uncertainty in the estimated marker 200 positions. This is analogous to the approach usually used to mitigate problems with uncertainty in GPS systems.

4) For determining a distance-dependent audio pitch, a suggested embodiment is to multiply the estimated position with the zone 170a, 170b, 170c, 170d shape. Alternatively, the region of uncertainty may be multiplied with the zone 170a, 170b, 170c, 170d shape. An integral, indicating the degree of belief in the angular disposition 180, 190, may be outputted as the volume of the tone, while the pitch of the tone may indicate a transverse and/or longitudinal disposition (distance). For example, an inverse relationship may be used between the pause duration between beeps—a shorter pause indicating a higher degree of proximity (or closeness).

The probe 100 may be further configured and arranged to determine a longitudinal and/or transverse disposition of the marker 200 with respect to an appropriate reference point on the probe 300, such as a distal end 160 of the probe 100.

The distance (longitudinal and/or transverse disposition) to the marker 200 may be estimated to a high degree of accuracy if probe 100 is first oriented such that it is pointing towards the marker 200.

When the probe 100 points to the marker 200, Br=−By (the Y-axis 700 of the probe 100 points to the marker 200, but r points from the marker 200 to the magnetic sensors 110, 120 comprised in the probe 100).

Since Bφ=0, the square of the magnitude of the field is given by:

$$|B|^2 = B_r^2 + B_\theta^2 = B_x^2 + B_y^2 + B_z^2$$

and $$|B_\theta| = \sqrt{|B|^2 - B_r^2} = \sqrt{B_x^2 + B_z^2}$$

From the equations above for $B_r$ and $B_\theta$:

$$\left(\frac{B_r^2}{2}\right) + B_\theta^2 = \left(\frac{|m|\cos\theta}{r^3}\right)^2 + \left(\frac{|m|\sin\theta}{r^3}\right)^2 = \left(\frac{|m|}{r^3}\right)^2$$

inserting the earlier expressions for Br and $|B_\theta|$, we get $$\left(\frac{|m|}{r^3}\right)^2 = \left(\frac{B_r^2}{2}\right) + B_\theta^2 = \left(\frac{B_y}{2}\right)^2 + B_x^2 + B_z^2$$

which gives a simpler expression for estimating r, $$r^3 = \frac{|m|}{\sqrt{\left(\frac{B_y}{2}\right)^2 + B_x^2 + B_z^2}}$$

This solution may be implemented with a variety of sensor arrangements, including this depicted in FIG. 1 and FIG. 2.

FIG. 2A to FIG. 2F depict further probe configurations which may be used with the invention.

Figure 2A:
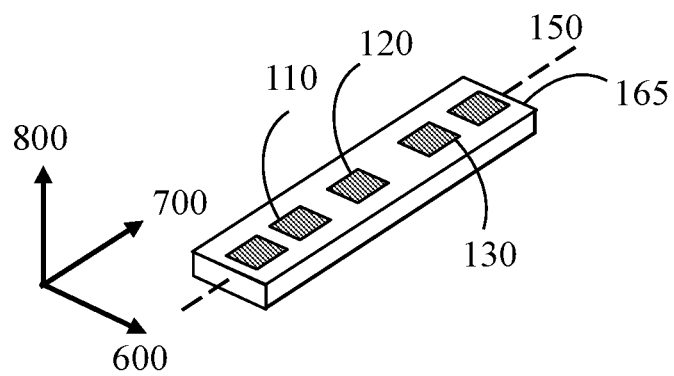
FIG. 2A to FIG. 2F depict further probe configurations which may be used with the invention.

For example:

FIG. 2A—magnetic field sensors 110, 120 are arranged substantially along a longitudinal axis or Y-axis 700. In this example, they are arranged along the probe longitudinal axis 150. They are arranged on a suitable substrate, such as a PCB. The substrate lies in a X-Y plane 600-700. One or more further sensors 130 may be disposed at the proximal end 165 may be provided to compensate for any background field, or to be configured and arranged to be at a major sensor separation from a sensor 1110, 120 closer to the distal end.

This may be considered a 1D geometry—magnetic field sensors are arranged substantially along an axis.

If the background field is not sufficiently uniform, or if the background field sensors pick up the dipole field of the marker (not depicted) (because the marker is close to the background field sensors), it may be advantageous to subtract the background field locally.

For example, by measuring the gradient of the B-field because the dipole field is varying over space, and assuming that the background field is uniform (at least over the range of the measurement; for example, the distance between two adjacent sensors). This approach may be used with a 3D array with sensitivity to curvature in all three directions 600, 700, 800.

A 3D array comprises magnetic field sensors arranged substantially along a plane, and further along at least one axis, substantially perpendicular to said plane. It may also comprise magnetic field sensors arranged substantially along first plane, and further along a second plane, substantially perpendicular to the first plane.

A further approach which may be used with a 2D array is described below. A 2D array comprises magnetic field sensors arranged substantially along a plane. For a uniform field, $\partial Br/\partial r$ and $\partial B\theta/\partial r=0$. This may be implemented by taking the difference of the field along the length of the probe (Y-axis 700 and/or longitudinal axis 150. It will be aligned with r when the probe is pointing at the magnet comprised in the marker. r is the −y direction and $|B\theta|=\sqrt{(B^2_x+B^2_z)}$.

For the dipole:

$$\frac{\partial Br}{\partial r} = -\frac{6|m|}{r^4}\cos\theta \text{ and } \frac{\partial B\theta}{\partial r} = -\frac{3|m|}{r^4}\sin\theta$$

then:

$$\left(\frac{1}{6}\frac{\partial Br}{\partial r}\right)^2 + \left(\frac{1}{3}\frac{\partial B\theta}{\partial r}\right)^2 = \left(\frac{|m|}{r^4}\right)^2$$

and r is given by:

$$r = \left[\frac{|m|^2}{\left(\frac{1}{6}\frac{\partial Br}{\partial r}\right)^2 + \left(\frac{1}{3}\frac{\partial B\theta}{\partial r}\right)^2}\right]^{1/4}$$

The partial derivative terms can then be approximated by:

$$\frac{\partial Br}{\partial r} \approx -\frac{B_{y1}-B_{y0}}{y1-y0} \text{ and } \frac{\partial B\theta}{\partial r} \approx -\frac{B_{\theta 1}-B_{\theta 0}}{y1-y0} \text{ where } B_\theta = B_x + B_z$$

Figure 2B:
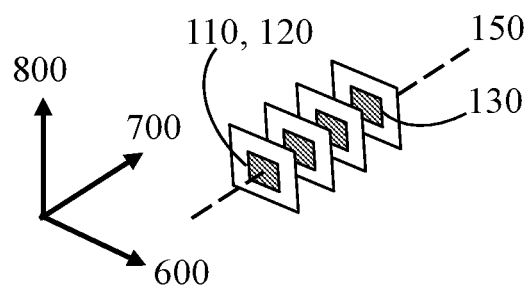

FIG. 2B—the sensors 110, 120, 130 are stacked such that they lie substantially along a longitudinal axis or Y-axis 700. In this example, they are arranged along the probe longitudinal axis 150. Each sensor may be on its own small PCB (which may have sensors on one or both sides)—each PCB is disposed in the XZ plane 600-800. This arrangement increases the packing density of sensors.

Figure 2C:
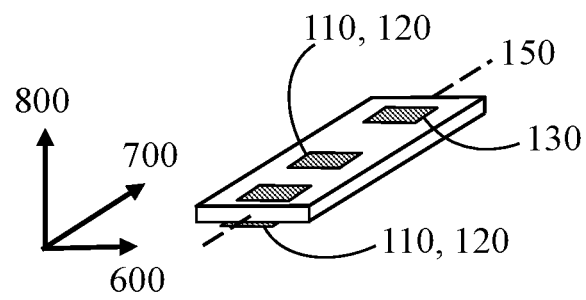

FIG. 2C—magnetic field sensors 110, 120, 130 are arranged substantially along a longitudinal axis or Y-axis 700. In this example, they are arranged along the probe longitudinal axis 150, similar to FIG. 2A. They are arranged on a suitable substrate, such as a PCB. The substrate lies in a X-Y plane 600-700. In this example, a 2D array is provided—a further row of sensors (only partially visible) is disposed along the underside of the substrate depicted. In other words, sensors 110, 120, 130 are provided at different dispositions along a transverse axis 800, but on both sides of the substrate. This arrangement increases the packing density of the sensors 110 and also allows the magnetic field gradient to be inferred. The magnetic field measurements of adjacent sensors 110, 120, 130 above and below may, for example, be averaged. This provides B-field vector measurements that are effectively along a line in space between the adjacent sensors 110, 120, 130.

Figure 2D:
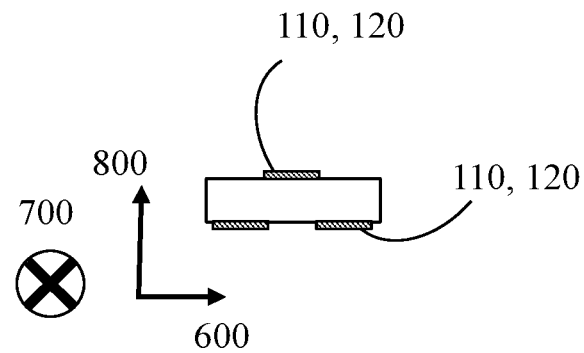

FIG. 2D—magnetic field sensors 110, 120 are arranged substantially along a longitudinal axis or Y-axis 700 (only partially visible). In this example, they are arranged along the probe longitudinal axis 150, similar to FIG. 2C. They are arranged on a suitable substrate, such as a PCB. The substrate lies in a X-Y plane 600-700. In this example, a 3D array is provided—two further rows of sensors (only partially visible) is disposed along the underside of the substrate depicted. In other words, sensors 110, 120 are provided at different dispositions along a transverse axis 800, but on both sides of the substrate. The sensors 110, 120 may also be considered to be grouped in threes in a triangular arrangement, lying in a X-Z plane 600-800—the sensors of only one group 110, 120 are visible.

Figure 2E:
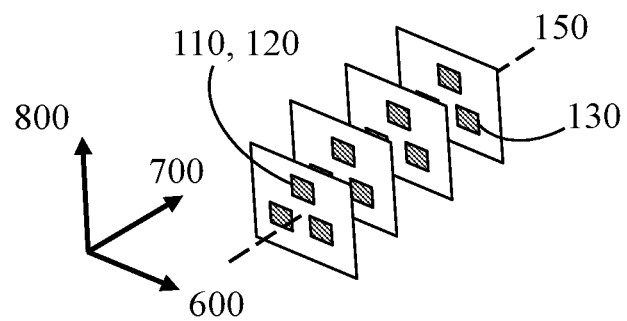

FIG. 2E—similar to FIG. 2B, the sensors 110, 120, 130 are stacked such that they lie, in groups of three in a triangular arrangement, each group being disposed on a PCB lying in an X-Z plane 600-800.

The PCB's are disposed substantially along a longitudinal axis or Y-axis 700. In this example, they are arranged along the probe longitudinal axis 150. Each sensor may be on its own small PCB (which may have sensors on one or both sides)—each PCB is disposed in the XZ plane 600-800. In other words, the sensors 110, 120, 130 are provided in a 3D array. This arrangement further increases the packing density of the sensors 110, 120 and also allows the magnetic field gradient to be inferred.

Figure 2F:
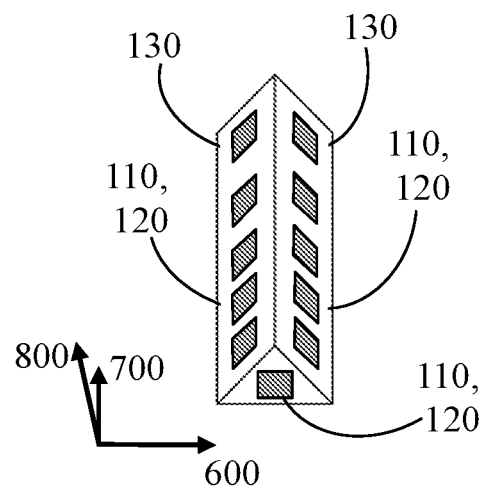

FIG. 2F—sensors 110, 120, 130 are disposed on three substrate sections, each extending along a longitudinal axis or Y-axis 700. The three substrate sections are mutually attached by their longitudinal edges, forming a hollow substrate arrangement with a triangular transverse 600-800 cross-section. arranged such that the transverse cross-section, in the X-Z plane, is triangular. In other words, a 3D array is provided using three 1D arrays of sensors, each 1D array being disposed on a separate substrate section, and with each 1D array of sensors being disposed along a longitudinal axis 700 substantially parallel to the longitudinal axis 700 of the probe.

This arrangement greatly increases the packing density of the sensors 110, 120 and also allows the magnetic field gradient to be inferred. It also allows a large number of sensors to be packed within a relatively cylindrical package, and also reduces the distance between the "front sensor" and the marker (not depicted).

Embodiment 2: 3D Sensor Array and Magnetic Field Strength Gradients

For a further embodiment of the probe, 100, 3D sensor grids 110, 120 may be used to measure spatial gradients of magnetic field intensity; for example the layouts depicted in FIG. 2D or FIG. 2E. Square/cubic grids are possible.

The magnetic field strength gives an estimate of the distance and the relative strength of the magnetic field between the left/right hand side sensors (and similarly for upper/lower) gives an estimate of the direction: if the seed is located towards the left, the left sensor will pick up a stronger signal than the right sensor. This difference can be used as a (relative) measure for lateral displacement. If the differences between left/right and up/down sensors are minimized, the wand is essentially pointing towards the marker.

Figure 6:
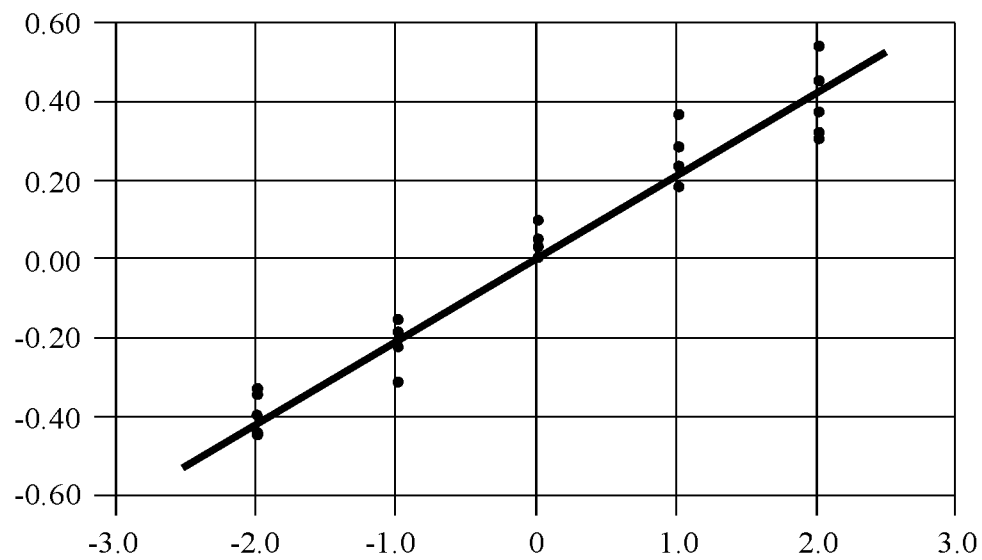
FIG. 6 depicts an example of differential measurement versus lateral displacement characteristic which may be used to convert the L-R signal from a sensor to lateral displacement.

FIG. 6 depicts an example of differential measurement versus lateral displacement characteristic which may be used to convert the L-R signal from a sensor to lateral displacement. From each sensor (L and R) the magnitude of the magnetic field is measured. Differential measurements are made by comparing field strengths at neighboring sensors. For example, left versus right; front versus back, top versus bottom. If the differential is zero, the marker 200 is disposed close to the middle point between the sensors. If the differential is positive, the marker is disposed more to the right. If the differential is negative, the marker is disposed more to the left.

The x-axis shows displacement X in centimeters (cm), from −3.0 to +3.0. The Y-axis shows the L-R signal from −0.60 to 0.60. Using a magnetic marker 200 which is cylindrical, made of NdFeB, 4 mm in length, and 2 mm in diameter, the L-R signal was measured at transverse dispositions of X=−2.0, −1.0, 0, +1.0 and +2.0—these are depicted as dots at those displacement values. These distances are in the range five to twenty times a dimension of the magnetic marker 200. At X=0, the magnetic marker 200 is disposed on the probe longitudinal axis 150. Based on these values, a characteristic has been fitted, which is a straight line from −2.5, −0.52775 to 2.5, 0.52775. In other words, the distance X may be calculated from L-R=0.2111X. In this example, the correlation factor ($R^2$) of the linear curve fit is 0.9328.

A further advantage of providing a software-configurable detection zone is that two or more marker detection zones may be configured, with differing extents, different shapes, different angular boundaries, different longitudinal extents, different transverse extents, and any combination thereof. These two or more marker detection zones may share one or more boundaries, be contiguous along one or more axes, be non-contiguous along one or more axes, or any combination thereof.

Figure 8A:
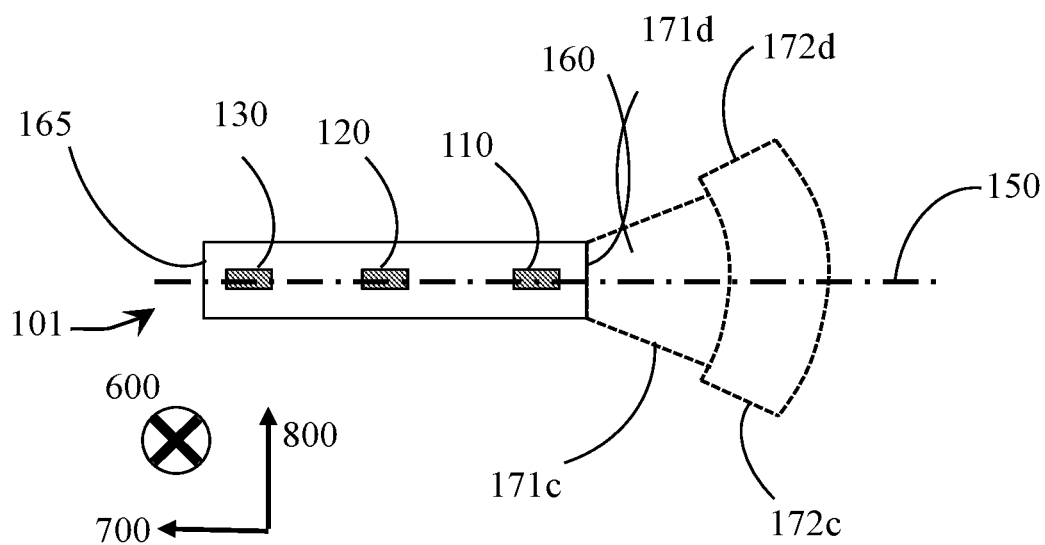
FIGS. 8A and 8B depict two examples of detections zones with different extents.
Figure 8B:
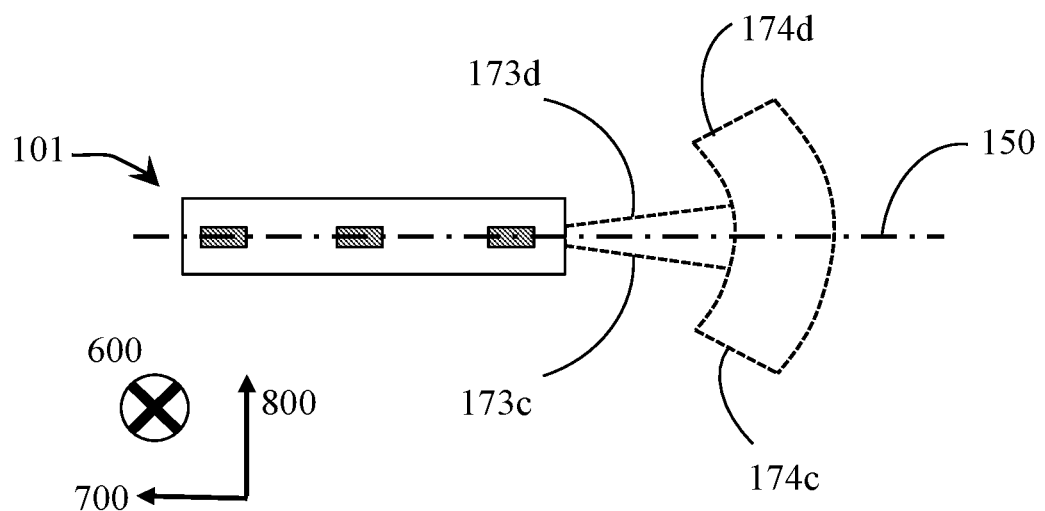

For example, FIG. 8A and FIG. 8B depict two examples of detections zones with more than different extents. The views shown and the probe 101 depicted are similar to the probe 100 depicted in FIG. 1B.

FIG. 8A depicts a second marker detection zone 171c, 171d extending from the distal end 160 along a probe longitudinal axis 150. Although depicted with a triangular cross-section in the YZ plane 700-800 and substantially symmetrical, this is not essential—any form of cross-section may be used.

The second marker detection zone may be mainly determined by two or more angular boundaries 171c, 171d as indicated by the dashed lines—for example, +/−22.5 degrees relative to the longitudinal axis 150. In other words, a marker detection angle of 45 degrees, disposed substantially symmetrical about the probe longitudinal axis 150.

Additionally and optionally, the distance between the two or more angular boundaries 171c, 171d proximate the distal end 160 of the probe 101 may be predetermined and/or controlled—for example, 18.5 mm. Additionally and optionally, the extent that the second marker detection zone extends along the longitudinal axis 150 away from the distal end 160 of the probe 101, depicted as a curved dashed line, may be predetermined or controlled—for example, 29 mm.

FIG. 8A further depicts a third marker detection zone 172c, 172d extending from the longitudinal extent of the second marker detection zone 171c, 171d, and extending further away from the distal end 160 from the probe 101.

Although depicted with an arc cross-section in the YZ plane 700-800 and substantially symmetrical, this is not essential—any form of cross-section may be used.

The third marker detection zone may be mainly determined by two or more angular boundaries 172c, 172d as indicated by the dashed lines—for example, +/−30 degrees relative to the longitudinal axis 150. In other words, a marker detection angle of 60 degrees, disposed substantially symmetrical about the probe longitudinal axis 150.

Additionally and optionally, the distance between the two or more angular boundaries 172c, 172d proximate the longitudinal extent of the second marker detection zone 171c, 171d—for example, 47 mm. Additionally and optionally, the extent that the third marker detection zone 172c, 172d extends along the longitudinal axis 150 away the longitudinal extent of the second marker detection zone 171c, 171d, depicted as a curved dashed line, may be predetermined or controlled—for example, 20 mm.

FIG. 8B depicts a fourth marker detection zone 173c, 173d extending from the distal end 160 along a probe longitudinal axis 150. Although depicted with a triangular cross-section in the YZ plane 700-800 and substantially symmetrical, this is not essential—any form of cross-section may be used.

The fourth marker detection zone may be mainly determined by two or more angular boundaries 173c, 173d as indicated by the dashed lines—for example, +/−10 degrees relative to the longitudinal axis 150. In other words, a marker detection angle of 20 degrees, disposed substantially symmetrical about the probe longitudinal axis 150.

Additionally and optionally, the distance between the two or more angular boundaries 173c, 173d proximate the distal end 160 of the probe 101 may be predetermined and/or controlled—for example, 5 mm. Additionally and optionally, the extent that the fourth marker detection zone extends along the longitudinal axis 150 away from the distal end 160 of the probe 101, depicted as a curved dashed line, may be predetermined or controlled—for example, 33 mm.

FIG. 8B further depicts a fifth marker detection zone 174c, 174d extending from the longitudinal extent of the fourth marker detection zone 173c, 173d, and extending further away from the distal end 160 from the probe 101.

Although depicted with an arc cross-section in the YZ plane 700-800 and substantially symmetrical, this is not essential—any form of cross-section may be used.

The fifth marker detection zone may be mainly determined by two or more angular boundaries 174c, 174d as indicated by the dashed lines—for example, +/−30 degrees relative to the longitudinal axis 150. In other words, a marker detection angle of 60 degrees, disposed substantially symmetrical about the probe longitudinal axis 150.

Additionally and optionally, the distance between the two or more angular boundaries 174c, 174d proximate the longitudinal extent of the fourth marker detection zone 173c, 173d—for example, 47 mm. Additionally and optionally, the extent that the fifth marker detection zone 174c, 174d extends along the longitudinal axis 150 away the longitudinal extent of the fourth marker detection zone 173c, 173d, depicted as a curved dashed line, may be predetermined or controlled—for example, 20 mm Additional marker detections zones may also be configured and arranged, with different degrees of special overlap. These may be substantially fixed, dynamic or any combination thereof. This may provide a coarse/fine marker detection zone configuration—for example, as the distal end 160 of the probe 101 gets closer (for example, less than 30 to 40 mm or less than approximately 35 mm) to the magnetic marker 200, a marker detection zone with a smaller angle may be automatically selected to further increase the accuracy, selectivity and sensitivity.

Another advantage of providing a software-configurable detection zone is that two or more marker detection zones may be defined, and the probe may be further configured and arranged to determine whether the angular disposition 180, 190 substantially coincides with:
- a first marker detection zone 170abcd, 1710cdb, 1720cd, 1730cd, 174cd;
- a second marker detection zone 170abcd, 1710cdb, 1720cd, 1730cd, 174cd;
- both the first and second detection zones 170abcd, 1710cdb, 1720cd, 1730cd, 174cd;
- neither the first or second detection zones 170abcd, 1710cdb, 1720cd, 1730cd, 174cd; or
- any combination thereof.

It becomes possible to modify the searching parameters in a way that is intuitive to the user by modifying one or more parameters or aspects associated with the one or more detection zones, such as, such as, for example, an extent, a shape, an orientation, a disposition, a scaling, a resolution, an angular boundary, a longitudinal extent, a transverse extent, and any combination thereof.

One or more configurable aspect of a detection zone may be determined automatically by the probe based on one or more measurements from one or more sensors and/or based on one or more suitable parameters. Additionally or alternatively, the user may provide one or more parameters to influence the determination.

Additionally or alternatively, the determination may be user selectable. It is particularly intuitive to use distinct detection zones, so that the user may modify their use of the probe—for example, larger and quicker movements may be encouraged with a "further away" detection zone, and smaller and slower movements with a "closer by" detection zone.

Additionally or alternatively, the user selection may be based on a treatment or therapy. Additionally or alternatively, the user selection may be based on an invasive or non-invasive use. Additionally or alternatively, the user selection may be based on use as a hand-held wand.

Additionally or alternatively, a user may choose a configuration particularly suited to, for example, the expected location of the marker in the human or animal body, the expected proximity, the expected magnetic field strength, and the expected marker orientation. The one or more marker detection zones may also be configured and arranged to adopt a certain configuration, depending on the expected (by the user) proximity and/or orientation to the marker. This may also be automated to a degree, depending on the measured and/or estimated proximity and/or orientation (by the probe). Any combination in different degrees is also possible.

Additionally or alternatively, the user may also select a configuration that they have personally found to be particular efficient for marker localization.

As the one or more detection zones may be configured in several dimensions, one or more of these shapes and cross-sectional shapes may be combined. Simple shapes may be used and/or complex shapes. A further advantage of providing a software-configurable detection zone is that a user may configure and arrange two or more marker detection zones. This may provide, for example, a coarse/fine marker detection zone configuration—as the distal end of the probe gets closer to the magnetic marker, a marker detection zone with a smaller angle may further increase the accuracy and sensitivity.

Additionally, the probe may comprise additional sensors to provide for measurement of the orientation of probe. For example, the pitch, roll and yaw angle of the probe from an IMU (inertial measurement unit) sensor, the orientation relative to the background magnetic field from the background field sensor or other inputs. This orientation may also be considered when determining the disposition of the magnetic marker 200 and/or when determining a configurable aspect of a detection zone.

Any other inputs that give position information may similarly be used—for example, an optical sensor, similar to the sensor used on an optical mouse, may be used to determine a contact point on the surface of the skin.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

Particularly advantageous embodiments may be summarized as follows:

A. A magnetic field probe (100, 101) for determining an angular disposition (180, 190) of an implantable marker (200), the marker (200) being configured to generate, in use, a magnetic field, the probe comprising:
- a distal end (160);
- a first magnetic sensor (110) close to the distal end (160);
- a second magnetic sensor (120), disposed between the first magnetic sensor (110) and a proximal end (165), the first and second magnetic sensors being configured and arranged to determine, in use, one or more magnetic field vectors of the marker (200);

the probe being further configured:
- to define one or more marker detection zones (170abcd, 171cd, 172cd, 173cd, 174cd), extending from the distal end (160) along a probe longitudinal axis (150);
- to determine the angular disposition (180, 190) to the implantable marker (200) using the one or more magnetic field vectors; and
- to determine whether the angular disposition (180, 190) substantially coincides with the one or more marker detection zones (170abcd, 171cd, 172cd, 173cd, 174cd).

B. The probe according to embodiment A, wherein the probe is further configured to determine whether the angular disposition (180, 190) substantially coincides with:
- a first marker detection zone (170abcd, 1710cdb, 1720cd, 1730cd, 174cd);
- a second marker detection zone (170abcd, 1710cdb, 1720cd, 1730cd, 174cd);
- both the first and second marker detection zones (170abcd, 1710cdb, 1720cd, 1730cd, 174cd);
- neither the first or second marker detection zones (170abcd, 1710cdb, 1720cd, 1730cd, 174cd); or
- any combination thereof.

Q. A detector unit for detecting the angular disposition of an implantable marker (200), the detector unit comprising the magnetic probe (100, 101) according to any of embodiments A to B.

R. A method for determining an angular disposition (180, 190) of an implantable marker (200), the marker (200) being configured to generate, in use, a magnetic field, the method comprising:

providing a probe (100, 101) with a distal end (160), the probe further comprising: a first magnetic sensor (110) close to the distal end (160); a second magnetic sensor (120), disposed between the first magnetic sensor (110) and a proximal end (165), the first and second magnetic sensors being configured and arranged to determine, in use, one or more magnetic field vectors of the marker (200);

configuring and arranging the probe to define one or more marker detection zones (170abcd, 171cd, 172cd, 173cd, 174cd), extending from the distal end (160) along a probe longitudinal axis (150);

determining the angular disposition (180, 190) to the implantable marker (200) using the one or more magnetic field vectors; and determining whether the angular disposition (180, 190) substantially coincides with the one or more marker detection zones (170abcd, 171cd, 172cd, 173cd, 174cd).

REFERENCE NUMBERS USED IN DRAWINGS

100 a first embodiment of a magnetic field probe
101 a second embodiment of a magnetic field probe
110 a first sensor
120 a second sensor
130 a third sensor
150 a probe longitudinal axis
160 a distal end of probe
165 a proximal end of probe
170a, 170b extent of marker detection zone in X-Y plane
170c, 170d extent of marker detection zone in Y-Z plane
171c, 171d extent of a second marker detection zone in Y-Z plane
172c, 172d extent of a third marker detection zone in Y-Z plane
173c, 173d extent of a fourth marker detection zone in Y-Z plane
174c, 174d extent of a fifth marker detection zone in Y-Z plane
180 an XY angular disposition
190 a YZ angular disposition
191 a first inclination θ
192 a second inclination θ
193 a third inclination θ
194 a fourth inclination θ
195 a fifth inclination θ
196 a sixth inclination θ
200 implantable magnetic marker or induced magnetic marker
300 an outer surface of skin
401 first magnetic field line
402 second magnetic field line
403 third magnetic field line
404 fourth magnetic field line
500 inclination relationship
550 inclination of probe
575 inclination of fields in probe plane
600 X-axis
700 Y-axis
800 Z-axis
900 magnetic marker axis
920 magnetic field
930 magnetic vector
950 transverse axis
970 detection position

The invention claimed is:

1. A magnetic field probe for determining an angular disposition of an implantable marker, wherein the implantable marker comprises a magnetic dipole configured to generate, in use, a magnetic field, the magnetic field probe comprising:
a distal end;
a first magnetic sensor at the distal end of the magnetic field probe;
a second magnetic sensor, disposed between the first magnetic sensor and a proximal end of the magnetic field probe; and
a processor, configured to collect measurement values from the first magnetic sensor and from the second magnetic sensor, and further configured and arranged to determine, in use, one or more magnetic field vectors of the magnetic dipole;
the processor being further configured:
to define two or more marker detection zones, extending from the distal end of the magnetic field probe along a probe longitudinal axis;
to determine the angular disposition to the magnetic dipole using the one or more magnetic field vectors;
to determine that the implantable marker falls within the one of the two or more marker detection zones if the angular disposition coincides with one of the two or more marker detection zones; and
to suppress one or more magnetic field vector determinations if the angular disposition to the magnetic dipole does not coincide with the one of the two or more marker detection zones.

2. The probe according to claim 1, wherein the two or more marker detection zones are symmetrical about the longitudinal axis.

3. The probe according to claim 1, wherein the two or more marker detection zones have a circular-, oval-, elliptical-, triangular-, rectangular-, or square-longitudinal cross-section perpendicular to the probe longitudinal axis.

4. The probe according to claim 1, wherein the two or more marker detection zones have an arc-, cylindrical or cone-shape.

5. The probe according to claim 1, wherein the two or more marker detection zones share one or more boundaries.

6. The probe according to claim 1, wherein the two or more marker detection zones differ by a parameter selected from the group consisting of:
an extent, a shape, an orientation, a disposition, a scaling, a resolution, an angular boundary, a longitudinal extent, a transverse extent, or any combination thereof.

7. The probe according to claim 1, wherein the processor is further configured:
to define a further marker detection zone, extending from the distal end of the magnetic field probe along a probe longitudinal axis; and
to determine if the angular disposition coincides with one of the three or more marker detection zones, thereby determining that the implantable marker falls within the one of the three or more marker detection zones.

8. The probe according to claim 1, wherein:
the processor is further configured
to define a further marker detection zone, extending from the distal end of the magnetic field probe along a probe longitudinal axis, and further configured
to determine if the angular disposition coincides with:
the further marker detection zone;
both the first and further marker detection zones;
both the second and further marker detection zones;
neither the first nor further marker detection zones;
neither the second nor further marker detection zones; or
any combination thereof.

9. The probe according to claim 1, wherein the processor is further configured and arranged to determine the angular disposition of the implantable marker with respect to the distal end of the magnetic field probe.

10. The probe according to claim 1, wherein the processor is further configured and arranged to determine the angular disposition of the implantable marker with respect to the longitudinal axis of the magnetic field probe.

11. The probe according to claim 1, wherein the probe comprises at least one further magnetic sensor, and wherein the first magnetic sensor, the second magnetic sensor and the at least one further magnetic sensor are comprised in one or more 1D, 2D, or 3D arrays.

12. The probe according to claim 1, wherein the distal end of the magnetic field probe is configured and arranged:
to be disposed proximate to an outer surface of skin,
to contact an outer surface of skin,
to be inserted through an outer surface of skin,
to be inserted into a body cavity, or
any combination thereof.

13. The probe according to claim 1, wherein the probe further comprises a sound transducer, configured and arranged to provide audio feedback, and wherein an audio characteristic of the audio feedback is configured by the processor to be different depending on if the angular disposition coincides with the first marker detection zone or if the angular disposition coincides with second marker detection zone.

14. The probe according to claim 1, wherein the two or more marker detection zones comprise a coarse marker detection zone and a fine marker detection zone, wherein the fine marker detection zone has a smaller angular extent than the coarse marker detection zone.

15. The probe according to claim 14, wherein the processor is further configured and arranged to select the fine marker detection zone if the distal end of the magnetic field probe is proximate the implantable marker.

16. The probe according to claim 1, wherein the processor is configured and arranged to determine one or more configurable aspect of the two or more marker detection zones based on:
one or more measurements from one or more magnetic sensors; one or more parameters provided by a user; a selection by a user; or any combination thereof.

17. The probe according to claim 1, wherein the processor is configured and arranged to determine one or more configurable aspect of the two or more detection zones based upon a selection by a user to choose:
a treatment or therapy; an invasive or non-invasive use; use as a hand-held wand; an expected location of the implantable marker; an expected proximity; an expected magnetic field strength of the magnetic dipole; an expected marker orientation; a personal preference; a combination of shapes and cross-sectional shapes of one or more marker detection zones; a combination of marker detection zones; an angular extent of one or more marker detection zones, or any combination thereof.

18. The probe according to claim 16, wherein the one or more configurable aspects of the two or more detection zones are an extent, a shape, an orientation, a disposition, a scaling, a resolution, an angular boundary, a longitudinal extent, a transverse extent, or any combination thereof.

19. A detector unit comprising the magnetic field probe according to claim 1, the detector unit further comprising a display, the processor being further configured and arranged to indicate to the user the results of the determination of the angular disposition on the display.

20. The detector unit according to claim 19, wherein the processor is further configured and arranged to indicate the first marker detection zone and the second marker detection zones on the display.

21. A method for determining an angular disposition of an implantable marker, wherein the implantable marker comprises a magnetic dipole configured to generate, in use, a magnetic field, the method comprising:
providing a magnetic field probe with a distal end, the magnetic field probe further comprising: a first magnetic sensor at the distal end of the magnetic field; a second magnetic sensor, disposed between the first magnetic sensor and a proximal end of the magnetic field probe, and a processor;
configuring the processor to collect measurement values from the first magnetic sensor and from the second magnetic sensor;
configuring and arranging the processor to determine, in use, one or more magnetic field vectors of the magnetic dipole;
configuring and arranging the processor to define two or more marker detection zones, extending from the distal end of the magnetic field probe along a probe longitudinal axis;
determining the angular disposition to the magnetic dipole using the one or more magnetic field vectors;
determining that the implantable marker falls within the one of the two or more marker detection zones if the angular disposition coincides with one of the two or more marker detection zones; and
suppressing one or more magnetic field vector determinations if the angular disposition to the magnetic dipole does not coincide with the one of the two or more marker detection zones.

* * * * *